(12) United States Patent
Ellis et al.

(10) Patent No.: US 11,305,032 B2
(45) Date of Patent: Apr. 19, 2022

(54) ULTRAVIOLET AIR IRRADIATION SYSTEM AND ULTRAVIOLET AIR IRRADIATION PROCESS

(71) Applicant: Stanley W. Ellis, Bakersfield, CA (US)

(72) Inventors: Stanley W. Ellis, Bakersfield, CA (US); Kanchana Sanjaya Guneseke Karunaratne, Escondido, CA (US); Melinda Hixon, Bakersfield, CA (US); Mitchell Caughron, Bakersfield, CA (US)

(73) Assignee: Stanley W. Ellis, Bakersfield, CA (US)

( * ) Notice: Subject to any disclaimer, the term of this patent is extended or adjusted under 35 U.S.C. 154(b) by 0 days.

(21) Appl. No.: 17/334,492

(22) Filed: May 28, 2021

(65) Prior Publication Data

US 2021/0369906 A1    Dec. 2, 2021

Related U.S. Application Data

(60) Provisional application No. 63/032,324, filed on May 29, 2020.

(51) Int. Cl.
*A61L 9/20*     (2006.01)
*A62B 18/08*    (2006.01)
(Continued)

(52) U.S. Cl.
CPC ............... *A61L 9/20* (2013.01); *A62B 7/10* (2013.01); *A62B 9/00* (2013.01); *A62B 18/006* (2013.01);
(Continued)

(58) Field of Classification Search
CPC .. A61L 9/20; A61L 2209/111; A61L 2209/12; A62B 9/00; A62B 18/006;
(Continued)

(56) References Cited

U.S. PATENT DOCUMENTS 2,920,622 A * 1/1960 Steel ................ A61M 15/02
                                                128/202.25
3,126,003 A * 3/1964 Steel ................ A61M 15/02
                                                128/204.16
(Continued)

FOREIGN PATENT DOCUMENTS

JP      2020044301 A  *  3/2020
WO  WO-2020035666 A1 *  2/2020 .............. C02F 1/325

*Primary Examiner* — Kathryn E Ditmer
(74) *Attorney, Agent, or Firm* — James M. Duncan; Scanlon Duncan LLP

(57) ABSTRACT

The present invention is a compact and portable personal ultraviolet air irradiation system having an ultraviolet air irradiation unit, a breathing tube, and a face mask. Unfiltered air passes through the ultraviolet air irradiation unit and is purified to ensure biological material has been neutralized by utilizing UV LEDs in the germicidal wavelengths of 100-280 nm. The ultraviolet air irradiation unit may further purify air of air particulates, gases, vapors, and biological material by utilizing a HEPA filter. The ultraviolet air irradiation unit may provide variable pressure to the mask to meet the breathing demands of the user. Flow through the ultraviolet irradiation unit may be reversible to irradiate the exhalations of a user who may be infected with a virus or other disease spread through exhalations.

25 Claims, 12 Drawing Sheets

(51) Int. Cl.
    *A62B 23/02* (2006.01)
    *A62B 18/00* (2006.01)
    *A62B 9/00* (2006.01)
    *A62B 7/10* (2006.01)
    *A62B 9/02* (2006.01)
    *A62B 18/10* (2006.01)

(52) U.S. Cl.
    CPC .............. *A62B 18/08* (2013.01); *A62B 23/02* (2013.01); *A61L 2209/111* (2013.01); *A61L 2209/12* (2013.01); *A62B 9/02* (2013.01); *A62B 18/10* (2013.01)

(58) Field of Classification Search
    CPC ......... A62B 18/08; A62B 23/02; C02F 1/325; A61M 15/02; F24F 8/22; A61G 13/108; A61G 10/02
    See application file for complete search history.

(56) References Cited

U.S. PATENT DOCUMENTS

| | | | | |
|---|---|---|---|---|
| 3,766,397 | A * | 10/1973 | Rockson | A47K 10/48 250/432 R |
| 5,612,001 | A * | 3/1997 | Matschke | A61L 2/10 250/455.11 |
| 5,833,740 | A * | 11/1998 | Brais | F24F 3/16 96/16 |
| 5,997,619 | A * | 12/1999 | Knuth | F24F 8/10 96/224 |
| 6,053,968 | A * | 4/2000 | Miller | A61L 9/20 96/16 |
| 6,470,888 | B1 * | 10/2002 | Matter | A61L 2/10 128/207.14 |
| 6,497,840 | B1 * | 12/2002 | Palestro | A61L 9/20 250/432 R |
| 11,052,169 | B1 * | 7/2021 | Pisharodi | A62B 9/00 |
| 2004/0184949 | A1 * | 9/2004 | McEllen | A61L 9/20 422/4 |
| 2004/0211321 | A1 * | 10/2004 | Gibson | F24C 15/20 96/381 |
| 2005/0000365 | A1 * | 1/2005 | Nelsen | A61L 9/20 96/224 |
| 2005/0045178 | A1 * | 3/2005 | Tang | A41D 13/0025 128/202.19 |
| 2005/0047975 | A1 * | 3/2005 | Tang | A61L 9/20 422/121 |
| 2005/0163648 | A1 * | 7/2005 | Liang | A61L 2/10 422/1 |
| 2005/0173352 | A1 * | 8/2005 | Burrows | B01D 53/007 96/224 |
| 2005/0242013 | A1 * | 11/2005 | Hunter | A61L 2/10 210/143 |
| 2006/0057020 | A1 * | 3/2006 | Tufo | F24F 3/16 422/24 |
| 2006/0060577 | A1 * | 3/2006 | Little | A61L 9/20 219/628 |
| 2006/0150819 | A1 * | 7/2006 | Yuen | A61L 9/22 96/224 |
| 2006/0177356 | A1 * | 8/2006 | Miller | A61M 11/06 422/121 |
| 2006/0231100 | A1 * | 10/2006 | Walker | A61M 16/08 128/205.25 |
| 2007/0101867 | A1 * | 5/2007 | Hunter | A62B 11/00 96/224 |
| 2007/0253860 | A1 * | 11/2007 | Schroder | B01D 53/8675 422/4 |
| 2007/0297951 | A1 * | 12/2007 | Caramuta | A61L 9/20 422/121 |
| 2008/0019861 | A1 * | 1/2008 | Silderhuis | F24F 8/192 422/3 |
| 2009/0050543 | A1 * | 2/2009 | Nishioka | C02F 1/008 210/87 |
| 2009/0205664 | A1 * | 8/2009 | Lyon | B01D 53/007 128/205.12 |
| 2010/0143205 | A1 * | 6/2010 | Engelhard | A61L 9/205 422/121 |
| 2010/0175694 | A1 * | 7/2010 | James | A61M 16/06 128/202.13 |
| 2010/0237254 | A1 * | 9/2010 | Mason | A61L 9/20 250/435 |
| 2010/0264329 | A1 * | 10/2010 | Vardiel | C02F 1/325 250/436 |
| 2010/0307332 | A1 * | 12/2010 | Yuen | B03C 3/60 95/26 |
| 2011/0114546 | A1 * | 5/2011 | Barsky | C02F 1/325 210/143 |
| 2011/0232481 | A1 * | 9/2011 | Worrilow | B01D 46/521 95/10 |
| 2012/0168641 | A1 * | 7/2012 | Lizotte | A61L 9/20 250/435 |
| 2012/0199003 | A1 * | 8/2012 | Melikov | F24F 3/163 95/273 |
| 2012/0299456 | A1 * | 11/2012 | Horng | F21K 9/232 313/46 |
| 2012/0315184 | A1 * | 12/2012 | Clark | A61L 9/20 422/4 |
| 2013/0128561 | A1 * | 5/2013 | Thomas | F21V 21/30 362/157 |
| 2013/0291735 | A1 * | 11/2013 | Livchak | F24F 1/01 96/224 |
| 2013/0307549 | A1 * | 11/2013 | Liu | G01J 1/0252 324/414 |
| 2014/0157989 | A1 * | 6/2014 | Kirschman | A61L 2/26 96/224 |
| 2014/0264072 | A1 * | 9/2014 | Abbott | A61M 16/1055 250/438 |
| 2015/0129776 | A1 * | 5/2015 | Boodaghians | C02F 1/325 250/432 R |
| 2015/0314024 | A1 * | 11/2015 | Khan | C02F 1/325 250/435 |
| 2016/0001108 | A1 * | 1/2016 | Zhou | A61L 9/00 128/863 |
| 2016/0213803 | A1 * | 7/2016 | Lunman | A61L 9/20 |
| 2016/0271288 | A1 * | 9/2016 | Davis | A61L 9/20 |
| 2016/0339133 | A1 * | 11/2016 | Lichtblau | A61L 2/24 |
| 2017/0007385 | A1 * | 1/2017 | Wang | A61C 19/004 |
| 2017/0217791 | A1 * | 8/2017 | McNulty | C02F 1/325 |
| 2018/0021471 | A1 * | 1/2018 | Krosney | A61F 7/0085 422/4 |
| 2018/0028846 | A1 * | 2/2018 | Hur | A62B 23/02 |
| 2018/0155215 | A1 * | 6/2018 | Torii | C02F 1/325 |
| 2018/0250430 | A1 * | 9/2018 | Machovina | B01D 53/0407 |
| 2018/0257953 | A1 * | 9/2018 | Mochizuki | G05D 7/0186 |
| 2018/0361007 | A1 * | 12/2018 | Caffrey | A61L 9/20 |
| 2019/0117820 | A1 * | 4/2019 | Dam | F24F 11/30 |
| 2019/0134251 | A1 * | 5/2019 | Jeong | F25D 17/042 |
| 2019/0233309 | A1 * | 8/2019 | Lu | C02F 1/008 |
| 2019/0247559 | A1 * | 8/2019 | Mochizuki | A61M 39/16 |
| 2019/0298868 | A1 * | 10/2019 | Kishi | B32B 5/026 |
| 2020/0171184 | A1 * | 6/2020 | Tanaka | A61L 2/10 |
| 2020/0338297 | A1 * | 10/2020 | Schuster | A61L 2/088 |
| 2020/0339441 | A1 * | 10/2020 | Wu | C02F 1/325 |
| 2021/0030914 | A1 * | 2/2021 | Muthuramalingam | A61L 9/205 |
| 2021/0206664 | A1 * | 7/2021 | Bilenko | A61L 9/18 |
| 2021/0260559 | A1 * | 8/2021 | Yamazaki | B29C 35/0805 |

* cited by examiner

ULTRAVIOLET AIR IRRADIATION SYSTEM AND ULTRAVIOLET AIR IRRADIATION PROCESS

FIELD OF INVENTION

The present invention relates generally to air filters and air purifiers. The present invention relates particularly, though not exclusively, to ultraviolet air irradiation systems and ultraviolet air irradiation processes. The present invention relates more particularly, though not exclusively, to personal ultraviolet air irradiation systems and ultraviolet air irradiation processes.

BACKGROUND OF THE INVENTION

Facial masks and respirators are worn in contaminated environments where the air is filled with pollution, particles, aerosols, and other harmful objects. Facial masks and respirators are manufactured to protect the user from the contaminated environment. Masks generally do not filter air of small particles but serve as a fluid barrier between the user and the environment. Masks prevent fluids in the form of large droplets, splashes, and sprays from contacting the covered area of the user. Masks cannot filter air of particulates, gases, or vapors. Respirators are designed to filter air of particulates, gases, and vapors.

Respirators reduce the risk of inhaling hazardous particulates, gases, and vapors by filtering air. Several different types of respirators exist and are specifically designed to work in different environments. Respirators are designed to filter the air of 95% to 100% of airborne particles. Additionally, respirators are designed to filter specific types of airborne particulates, gases, and chemical vapors. Respirators are also designed to be resistant to oils, which may degrade the filtering capability of the respirators. Respirators may also provide mechanical assistance to filter the incoming air or may provide its own clean air source. However, respirators are only capable of filtering airborne particulates, gases, or vapors.

Respirators only filter and cannot neutralize biological material that may reside in the air in the form of particulates. Respirators are rated at certain filter efficiencies under controlled laboratory tests and even under these conditions respirators rated at a 95% filter efficiency rating may allow up to 5% of airborne particulates, gases, and vapors to pass through the respirators. Moreover, it is statistically possible that a 100% filter efficiency may still allow airborne particulates, gases, and vapors to pass through the respirator. As a result, it is possible for the user to inhale the airborne particulates, gases, and/or vapors that pass through the respirator. In circumstances where the inhaled air may contain biological material, such as viruses, bacteria, or mold, the user may become sick as a result.

In light of the above, it would be advantageous to provide a system and process for filtering air of airborne particulates, gases, and vapors and eradicating any remaining biological material in the filter air prior to inhalation by a user. It would further be advantageous to provide a portable, compact, and lightweight system and process for filtering and eradicating biological material in the air prior to inhalation by a user of the system. Further, it would be advantageous to ensure that the system is adjustable to meet respiratory demands. Finally, it would be advantageous for the system to complete the eradication process without increasing respiratory effort which is typically required by conventional respirators.

SUMMARY OF INVENTION

The present invention is a system and process for filtering and irradiating incoming air to eliminate substantially all of any living biological matter contained in the air. The present invention, an ultraviolet air irradiation system, is designed to provide extensive protection through day-to-day operations. The ultraviolet air irradiation system purifies an incoming stream of biological material by utilizing ultraviolet light emitting diodes (hereinafter "UV LEDs") in the germicidal wavelengths of 100-400 nm. The incoming air stream may be optionally filtered utilizing a high efficiency particulate air (hereinafter "HEPA") filter to eliminate air particulates, gases, and vapors.

The system may be powered by an internal rechargeable battery pack to provide power to the system components, including UV LEDs and a pressure differential device such as a fan or vacuum pump. The pressure differential device provides a pressure differential which propels a stream of air through the system. The stream of air may first pass through a HEPA filter to reduce the number of harmful particulates entering the system. The air stream introduced into the system passes through a chamber which may comprise chamber walls comprising a reflective material, such as a reflective coating on the chamber walls. The chamber receives ultraviolet light from a plurality of UV LEDs, with the reflective material configured to bounce the rays of the UV LEDs within the chamber in order to maximize germicidal effectiveness. The irradiated air stream exits the chamber, and may be transmitted to a face mask where a user may inhale the irradiated air. The face mask helps separate the user from unpurified air in the surrounding environment. The face mask has an exit valve or other exhaust mechanism which allows exhaled air to leave the system. The ultraviolet air irradiation system may provide a variable air flow rate to the face mask to adapt to the user's need. The ultraviolet air irradiation system may also include a reversible function to purify the user's exhalations before purging those vapors from the ultraviolet air irradiation system, while taking in clean air from the surrounding environment.

In one embodiment of the present invention, the system comprises a portable personal ultraviolet air irradiation system having an ultraviolet air irradiation unit, a breathing tube, and a face mask. The ultraviolet air irradiation unit may be connected to the face mask with the breathing tube allowing air flow from the ultraviolet air irradiation unit to the face mask. Ambient air enters the ultraviolet air irradiation unit, which optionally filters the air to collect particulate matter, and then irradiates the air to ensure biological material has been neutralized. The irradiated and optionally filtered air flows through the breathing tube and into a face mask. The irradiated and optionally filtered air is inhaled by the user with exhalations exhausted through the face mask. The face mask may be initially sterilized which allows the user to remain isolated from the surrounding contaminated environment. The face mask thus provides the user with irradiated air and optionally filtered air free of air particulates, gases, vapors, and/or biological material.

Embodiments of the ultraviolet air irradiation unit may purify air of air particulates, gases, vapors, and/or biological material by utilizing, in combination, a HEPA filter with a high minimum efficiency reporting value (hereinafter "MERV") and UV LEDs in the germicidal wavelengths of 100-400 nm, and typically in the range of 100-280 nm.

When equipped with the optional HEPA filter, the ultraviolet air irradiation unit filters air of air particulates, gases, vapors, and/or biological material by passing air through the HEPA filter. The ultraviolet air irradiation unit purifies the filtered air by eradicating biological material, such as fungi, viruses, and/or bacteria by utilizing UV LEDs in the germicidal wavelengths of 100-280 nm to irradiate the air. It is noted that UV LEDs emitting light in the wavelengths of 100-280 nm are generally referred to as UV-C LEDs.

The ultraviolet air irradiation unit may be powered by an internal rechargeable battery pack which provides power to the ultraviolet air irradiation unit. The ultraviolet air irradiation unit may include a chamber housing UV-C LEDs, a device for applying differential pressure across the chamber, such as a unit fan or vacuum pump, and an optional HEPA filter. The ultraviolet air irradiation unit may be configured to be compact, lightweight, portable and self-contained thereby allowing the user to carry and operate the system throughout the day. The ultraviolet air irradiation unit may be configured as a backpack, fanny pack, or other attachable configuration allowing the user to carry the unit without inhibiting the user's movements. Embodiments of the ultraviolet air irradiation unit may be charged via USB or wearable solar device, such as a shirt containing solar panels for convenient on-the-go power.

In some embodiments of the invention, the pressure differential device causes a stream of air to flow into the unit and through the optional HEPA filter, which filters and reduces the number of harmful particulates entering the unit. The filtered air flows through the chamber housing which then receives ultraviolet light from the UV-C LEDs. The chamber comprises a material having a reflective surface which is configured to cause the UV-C light to be reflected so as to maximize the germicidal effectiveness of the ultraviolet air irradiation unit. In one embodiment of the invention, the air stream may be irradiated and then pass through an optional filter without departing from the spirit and scope of the invention. The purified air may then be delivered through the breathing tube to the face mask where the user is able to inhale the purified air.

The pressure differential apparatus of embodiments of the ultraviolet air irradiation unit provides a positive air flow to the face mask to provide the user with comfortable breathing and to prevent the backflow of air into the ultraviolet air irradiation unit. The differential pressure provided by the ultraviolet air irradiation unit coupled with an optional exit valve in the face mask facilitates the evacuation of the user's exhalations from the system. The ultraviolet air irradiation system thus provides a safe environment for the user while operating in a contaminated environment and provides the user with constant and consistent purified air to inhale. Embodiments of the ultraviolet air irradiation system may provide a variable air flow rate to adapt to the user's need. Embodiments of the ultraviolet air irradiation system may also comprise a reversible flow function which purifies the user's exhalations prior to releasing the exhalations into the atmosphere, thereby purifying the exhalations into the surrounding environment. This function eliminates or reduces the possibility that someone infected with a contagious disease spreads the disease to those around that person, thereby providing a means of protecting the general public from a person infected with a contagious disease.

BRIEF DESCRIPTION OF THE FIGURES

The objects, features, and advantages of the invention will be more clearly perceived from the following detailed description, when read in conjunction with the accompanying drawings, in which.

DETAILED DESCRIPTION OF THE INVENTION

Figure 1:
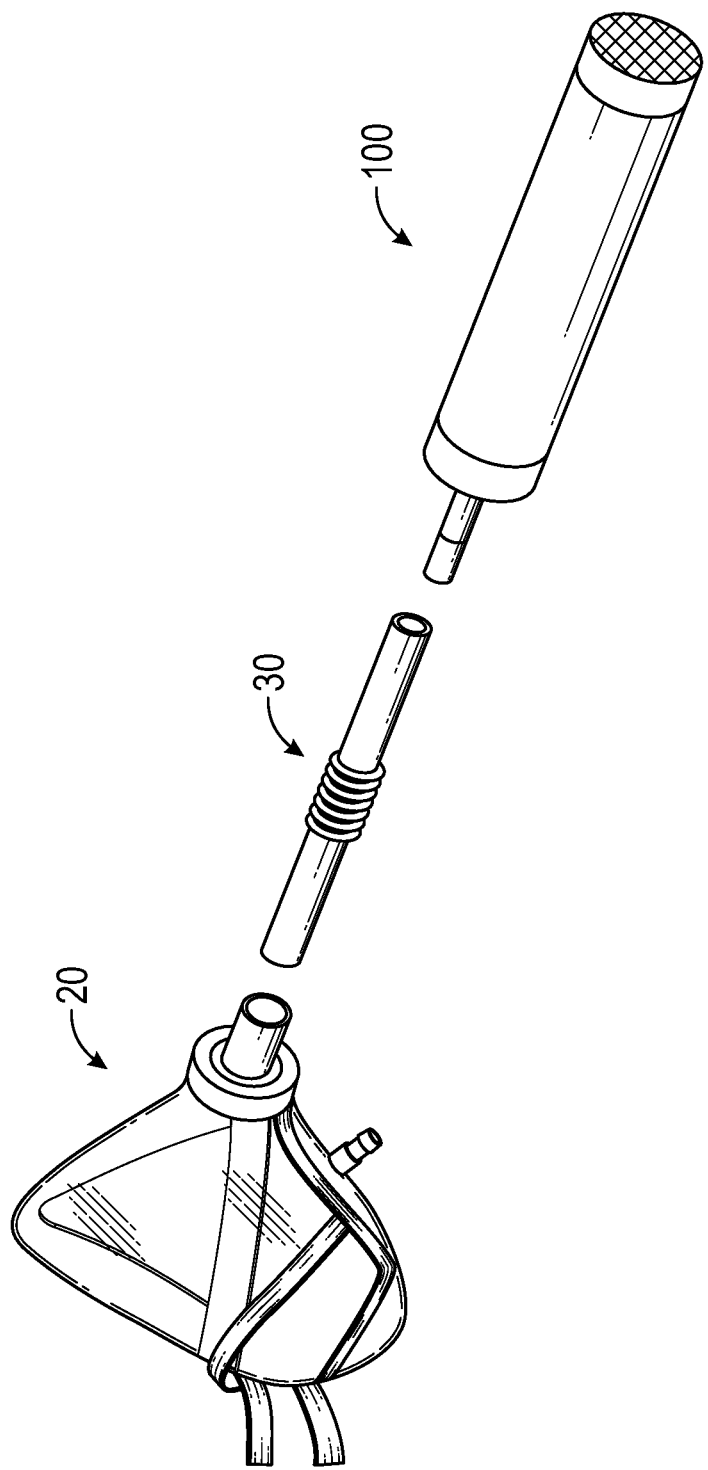
FIG. 1 depicts a perspective view of an embodiment of components of an embodiment of an ultraviolet air irradiation system having an ultraviolet air irradiation unit, a breathing tube, and a face mask.

Referring initially to FIG. 1, an embodiment of an ultraviolet air irradiation system is shown and generally designated 10. This embodiment of the ultraviolet air irradiation system 10 includes an ultraviolet air irradiation unit 100, a face mask 20, and a breathing tube 30. Embodiments of the ultraviolet air irradiation system 10 may purify air by both filtering and irradiating the air to remove or reduce any particulates and to substantially eliminate any living biological matter in the air. Embodiments of the ultraviolet air irradiation system 10 may provide extensive protection through day-to-day operations. Embodiments of the ultraviolet air irradiation system 10 may purify air of air particulates, gases, vapors, and/or biological material by utilizing an optional HEPA filter with a high minimum efficiency reporting value ("MERV") and by utilizing UV LEDs in the germicidal wavelengths which are known to be in the range of 100-400 nm. Embodiments of the ultraviolent air irradiation system 10 may comprise a monitoring system to monitor the air composition within the system, such as the oxygen and carbon dioxide levels.

In a first embodiment of the ultraviolet air irradiation system 10, an air stream is introduced into the ultraviolet air irradiation unit 100 which sequentially purifies the air by first filtering and then, or simultaneously, irradiating the air. In this embodiment, a HEPA filter filters the air to reduce the number of harmful particulates entering the ultraviolet air irradiation system 10. The air is also irradiated in the ultraviolet air irradiation unit 100 thereby eliminating harmful biological material. The purified air stream is thereafter delivered to the face mask 20 through the breathing tube 30 for inhalation by the user.

Embodiments of face mask 20 help separate or isolate the user from unpurified air in a surrounding environment. Embodiment of face mask 20 may have an exit valve or other exhaust mechanism which allows exhaled air to leave the mask. The ultraviolet air irradiation unit 100 provides positive air pressure to the face mask 20 thereby providing the user with comfortable breathing and preventing backflow of air into the ultraviolet air irradiation unit 100. The positive pressure provided by the ultraviolet air irradiation unit 100 coupled with an exit valve in the face mask 20 facilitates the evacuation of the user's exhalations from mask 20.

Embodiments of the ultraviolet air irradiation system 10 may be utilized to separate the user from a contaminated environment and provide the user with constant and consistent purified air to inhale. Embodiments of the ultraviolet air irradiation system 10 may include a variable air flow rate to adapt to the user's needs. The ultraviolet air irradiation system 10, specifically the ultraviolet air irradiation unit 100 and face mask 20, may comprise a reverse flow function which purifies the user's exhalations through the air irradiation unit 100 before releasing the exhalations into the environment. This function allows the a user to effectively be "quarantined" to prevent those around the user from being exposed to biologic materials, viruses, etc., contained in the user's exhalations. Embodiments of the ultraviolet air irradiation system 10 may be compact, portable, and lightweight allowing a user to carry and use the ultraviolet air irradiation system 10 for extensive protection through day-to-day operations. Embodiments of the ultraviolet air irradiation system 10 may also be sized to fit securely in a standard vehicle cupholder.

Embodiments of the ultraviolet air irradiation unit 100 may purify incoming air streams of air particulates, gases, vapors, and/or biological material by utilizing a HEPA filter with a high MERV and by utilizing UV LEDs in the germicidal wavelengths of 100-400 nm, and typically in the range of 100-280 nm. In some embodiments of the ultraviolet air irradiation unit 100, an incoming air stream is first filtered of air particulates, gases, vapors, and/or biological material by passing air through the HEPA filter. The ultraviolet air irradiation unit 100 uses UV radiation to irradiate the filtered air and neutralize biological material, such as fungi, viruses, and/or bacteria.

Figure 2:
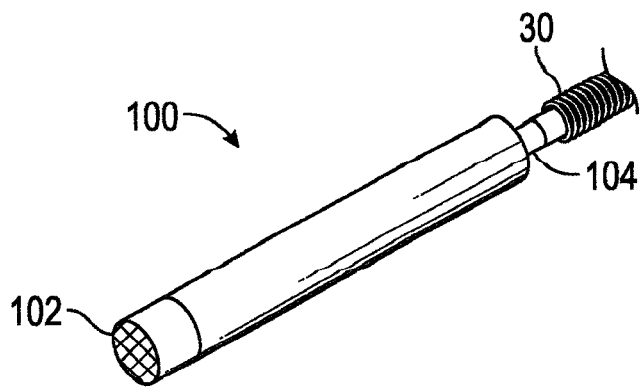
FIG. 2 depicts a perspective view of an embodiment of the ultraviolet air irradiation unit of FIG. 1.

Referring now to FIG. 2, a perspective view of an embodiment of an ultraviolet air irradiation unit 100 is shown. As shown, this embodiment of the ultraviolet air irradiation unit 100 includes an inlet 102 at one end and an outlet 104 at the opposite end. An unfiltered air stream may enter the ultraviolet air irradiation unit 100 at inlet 102. In this embodiment of the invention, the unfiltered air stream is purified by the ultraviolet air irradiation unit 100 by undergoing a filtering and an irradiation process. Filtered and irradiated air exits the ultraviolet air irradiation unit 100 at the outlet 104 and thereafter may enter the breathing tube 30. The filtered and irradiated air is thereafter delivered through breathing tube 30 to the face mask 20, as shown in FIG. 1, for inhalation by the user. The face mask 20 and the breathing tube 30 are typically sterile and air tight, thereby reducing the risk of contamination of the filtered and irradiated air stream exiting the ultraviolet air irradiation unit 100. A sterile face mask 20 and breathing tube 30 protects the user from the contaminated environment which utilizing the protective equipment in the first place.

Figure 3:
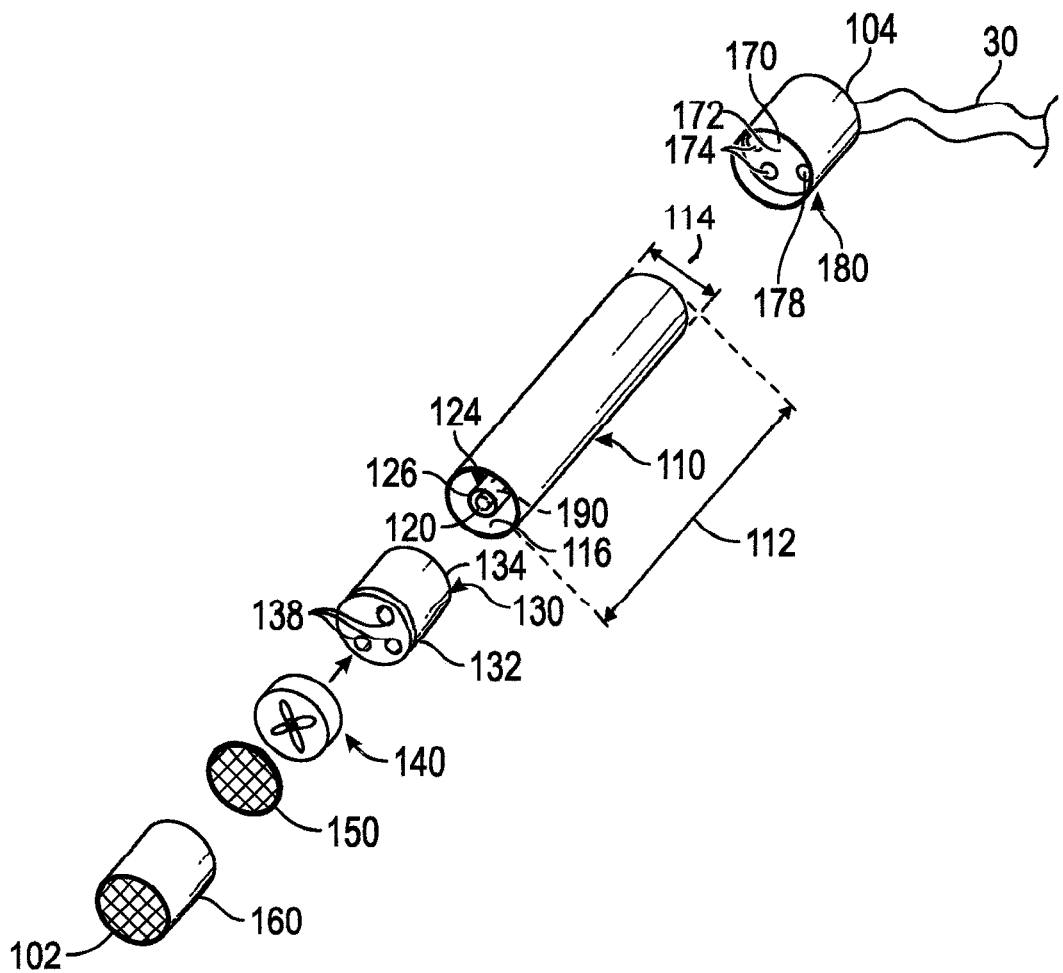
FIG. 3 depicts an exploded view of an embodiment of the ultraviolet air irradiation unit.

Referring now to FIG. 3, an exploded view of an embodiment of the ultraviolet air irradiation unit 100 is shown. In this embodiment, ultraviolet air irradiation unit 100 comprises a chamber 110, internal storage compartment 120, a first UV LED apparatus 130, a pressure differential apparatus hereinafter referred to as system fan 140 (it being understood that other pressure differential devices known in the art may be utilized in different configurations, such as a vacuum pump), a HEPA filter element 150, a first end cap 160, a second UV LED apparatus 170, and a second end cap 180.

Embodiments of the ultraviolet air irradiation unit 100 may include additional components and capabilities to monitor the operation of the ultraviolet air irradiation system 10 without departing from the spirit and scope of the present invention, including components to monitor the oxygen and carbon dioxide levels in the system.

The ultraviolet air irradiation unit 100 fits the filtering and irradiating components into a compact, lightweight, and portable unit. In an embodiment of the ultraviolet air irradiation unit 100, the ultraviolet air irradiation unit 100 may comprise a tubular configuration. This configuration facilitates carrying embodiments of the ultraviolet air irradiation unit 100 in the hand, in a pocket, use with a sling to carry over the shoulder, or placement of embodiments of the ultraviolet air irradiation unit in a conventional cup holder in a vehicle.

Embodiments of the ultraviolet air irradiation unit 100 may comprise a chamber 110 in a tubular configuration having a length 112 and a diameter 114. The internal wall 116 of the chamber 110 comprises a reflective material capable of reflecting ultraviolet radiation in the wavelengths of 100-400 nm, such as aluminum. Within embodiments of chamber 110, the internal storage compartment 120 may store the power source 190. The internal storage compartment 120 may comprise a tube having a length (not shown) and a diameter 124. The length of the internal storage compartment 120 may equal the length 112 of the chamber 110. The external wall 126 of the internal storage compartment 120 may comprise a reflective material capable of reflecting ultraviolet radiation in the wavelengths of 100-400 nm, which may again comprise aluminum. The reflective material of the chamber 110 and the internal storage compartment 120 are typically the same to provide even reflective properties along the length of the ultraviolet air irradiation unit 100.

Due to the reflective surfaces of the reflective materials of the chamber 110 and the internal storage compartment 120, any UV radiation in the void between the chamber 110 and the internal storage compartment 120 will bounce between the reflective surfaces. By utilizing a tube for the chamber 110, a smooth continuous reflective surface may be provided to facilitate evenly reflected UV radiation which is evenly reflected and directed towards the axial center of the chamber 110 where the internal storage compartment 120 is located. Utilization of a tubular configuration for the storage compartment 120 provides a smooth continuous reflective surface thereby providing evenly reflected UV radiation which is directed outwards back towards the interior wall 116 of the chamber 110. The utilization of tubular configurations for the chamber 110 and internal storage compartment 120 comprising UV reflective materials provides optimal distribution of UV radiation without dead spots caused by irregular surface patterns, such as corners or other angled surfaces.

One end of the chamber 110 may comprise first UV LED apparatus 130. The first UV LED apparatus 130 may have a circular base 132, multiple UV LEDs 134 (configured similarly as shown for LEDs 174 in second UV LED apparatus 170), electronic controls for operating the UV LEDs 134, and multiple air passageways 138. A system fan 140 may be disposed adjacent to the first UV LED apparatus 130. The system fan 140 provides the required pressure differential to cause positive air flow through the ultraviolet air irradiation unit 100 and delivery to mask 20. System fan 140 (and other pressure differential devices) may have the capability of providing variable air flow rates.

In this embodiment, HEPA filter element 150 may be adjacent to system fan 140. The HEPA filter element 150 has a high MERV. The HEPA filter element 150 is not restricted to a single type of filter and may be interchangeable to meet certain requirements, such as a 95%-100% filter rating, use in environments with oil, and use for specific hazardous environments. If the HEPA filter element 150 becomes saturated, it may be replaced with a new unused HEPA filter element 150. First end 160 may be formed with the air inlet 102 and may be configured to house the first UV LED apparatus 130, the system fan 140, and the filter element 150 and to enclose the first end of the chamber 110. First end cap 160 forms a seal with the exterior of the chamber 110 to control and direct an air flow into the ultraviolet air irradiation unit 100 through the air inlet 102. For this embodiment, this configuration provides for the filtering of air entering the ultraviolet air irradiation unit 100 by the HEPA filter element 150.

The opposite end of chamber 110 may comprise second UV LED apparatus 170. Second UV LED apparatus 170 may have a circular base 172, multiple UV LEDs 174, controls for operating the UV LEDs 174, and air passageway 178. The second end cap 180 comprises air outlet 104 and may be configured to house the second UV LED apparatus 170 and to enclose the second end of the chamber 110. The air passageway 178 is aligned with the air outlet 104. Second end cap 180 forms a seal with the exterior of the chamber 110 to control and direct a stream of air out of the ultraviolet air irradiation unit 100 through the air outlet 104, directing air exiting the ultraviolet air irradiation unit 100 to breathing tube 30.

As indicated in FIG. 3 first end cap 160 and second end cap 180 may be configured to sandwich chamber 110 and the internal compartment storage 120 between the first UV LED apparatus 130, the system fan 140, and the HEPA filter at one end and the second UV LED apparatus 170 at the opposite end. The internal compartment storage 120 may comprise a power source 190 which powers the electronic components.

This embodiment of the ultraviolet air irradiation unit 100 may purify air of air particulates, gases, vapors, and biological material by utilizing the HEPA filter element 150 with a high MERV and by utilizing the UV LEDs 134,174 which emit light in the germicidal wavelengths of 100-400 nm, typically in the range of 100-280 nm. The HEPA filter element 150 filters an air stream of air particulates, gases, vapors, and biological material. The ultraviolet air irradiation unit 100 irradiates the air to neutralize biological material, such as fungi, viruses, and bacteria by utilizing UV LEDs 134, 174 which generate light in the germicidal wavelengths.

Embodiments of the ultraviolet air irradiation unit 100 may be powered by an internal battery pack 190 which may be utilized to provide power to the ultraviolet air irradiation unit 100. Internal battery pack 190 may be rechargeable and embodiments of the battery pack may be charged via USB at home, in the car, or on the go. Alternatively, embodiments of the rechargeable battery pack may also be charged via solar panels, which may be configured on an exterior surface of a carrying case or on garments worn by the user, such as a shirt containing solar panels for convenient on the go power. The system fan 140, or other pressure differential apparatus, causes air flow from the air inlet 102 through an optional HEPA filter element 150, which may be used to filter and reduce the number of harmful particulates entering the unit. The filtered air thereafter flows through the air passageways 138 of the first UV LED apparatus 130 into the chamber 110. The chamber 110 comprises a reflective material, such as a reflective coating to bounce the UV radiation between the interior wall 116 of the chamber 110 and the exterior wall 126 of the internal storage compartment 120 to maximize the germicidal effectiveness of the ultraviolet air irradiation unit 100.

The ultraviolet air irradiation unit 100 may be connected to face mask 10 with breathing tube 30 providing air flow from the ultraviolet air irradiation unit 100 to the face mask 30. Filtered and irradiated air may flow through air passageway 178 of the second UV LED apparatus 170 and through the air outlet 104 of the second end cap 180. The filtered and irradiated air flows through breathing tube 30 and into the face mask 20. The filtered and irradiated air may thereafter be inhaled by the user with the user's exhalations exhausted through the face mask 20. The face mask 20 and breathing tube 30 may be sterile and not exposed to the contaminated environment, thereby providing the user with filtered and irradiated air free of air particulates, gases, vapors, and biological material.

In one embodiment of the ultraviolet air irradiation unit 100, the length 112 of the chamber 110 and the length 122 of the internal storage compartment 120 may be 300 mm, the diameter 114 of the chamber 110 may be 75 mm and the diameter 124 of the internal storage compartment 120 may be 25 mm. The first UV LED apparatus 130 may comprise three UV LEDs 134 (configured the same as LEDs 174 in second UV LED apparatus 170). Second UV LED apparatus 170 may also comprise three UV LEDs 174 for a total of six UV LEDs in the ultraviolet air irradiation unit 100. The UV LEDs 134, 174 are UV-C LEDs and may emit UV radiation in the wavelength range of 100-280 nm. More specifically, the UV-C LEDs may emit UV radiation in the range of 260-270 nm, with each having an output power of 60 mW. The first UV LED apparatus 130 may have the UV LEDs 134 configured in a circle with a radius of 18.75 mm and the second UV LED apparatus 170 may have the UV LEDs 174 configured in a circle with a radius of 18.75 mm. The first UV LED apparatus 130 and the second UV LED apparatus 170 may be configured to fit over the ends of the chamber 110 so the placement of the UV LEDs in a circle with a radius of 18.75 mm places the UV LEDs in the void between the chamber 110 and the internal storage compartment 120. The first UV LED apparatus 130 may be rotated 60° from the second UV LED apparatus 170 so that the UV LEDs 134 of the first UV LED apparatus 130 and the UV LEDs 174 of the second UV LED apparatus 170 do not overlap.

The surfaces of the chamber 110 and the internal storage compartment 120 comprise a reflective material which takes advantage of the radiation pattern of the UV LEDs 134,174. The radiation pattern of the UV LEDs 134 and 174 may be configured to be generally spherical. By positioning the UV LEDs 134 and 174 on either end of the chamber 110 and perpendicular to the interior wall 116 of the chamber 110 and the internal storage compartment 120, the UV radiation emitted from the sides of the UV LEDs 134 and 174 are reflected back towards the center. As a result, the interior wall 116 of the chamber 110 sees a peak irradiance of 9 mW/cm$^2$ total power 18.7 mW and the exterior wall 126 of the internal storage compartment 120 sees a peak irradiance 34 mW/cm$^2$, total power 28.3 mW. The total irradiance of the ultraviolet air irradiation unit 100 is approximately 10 mW/cm$^2$ along the length, so 6 seconds of exposure in the ultraviolet air irradiation unit 100 gives approximately 60 mJ/cm$^2$, which neutralizes approximately 99.99% of biological material in the air. Embodiments of the ultraviolet air irradiation unit 100 may thus provide a compact, portable, and lightweight system to purify air with minimal cost and components.

It is contemplated that the dimensions of the chamber 110, the internal storage compartment 210, and the number of UV LEDs 134 and 174 may be modified without departing from the spirit and scope of the invention to meet the desired specifications. The chamber 110 and the internal storage compartment 210 may be lengthened to increase the exposure of the air traveling at a constant velocity through the unit 100 to increase the irradiation. Alternatively, the number of UV LEDs 134 and 174 may be increased to increase the total power of the ultraviolet air irradiation unit 100.

The purified air, which is irradiated and optionally filtered, flows through the air passageway 178 of the second UV LED apparatus 178 and out the air outlet 104 and into the breathing tube 30. The purified air flows to the face mask 20 through the breathing tube 30 where the user is able to inhale the purified air. Utilizing a pressure differential apparatus, such as system fan 140, vacuum pump, etc., the ultraviolet air irradiation unit 100 provides positive air pressure to the face mask 20 to provide the user with comfortable breathing and to prevent the backflow of air into the ultraviolet air irradiation unit 100. The differential pressure provided by the ultraviolet air irradiation unit 100 may be coupled with an exit valve in the face mask 20 to facilitate evacuation of exhalations from the user through the exit valve and out of the ultraviolet air irradiation system 10. The ultraviolet air irradiation system 10 helps separate the user from the contaminated environment and provides the user with purified air to inhale. The ultraviolet air irradiation unit 100 may have a variable air flow rate to adapt to the users' need. The ultraviolet air irradiation unit 100 and face mask 20 may also include a reversible function to purify the user's exhale before purging it from the ultraviolet air irradiation system, thereby protecting others from any impurities contained within the exhalations.

Figure 4:
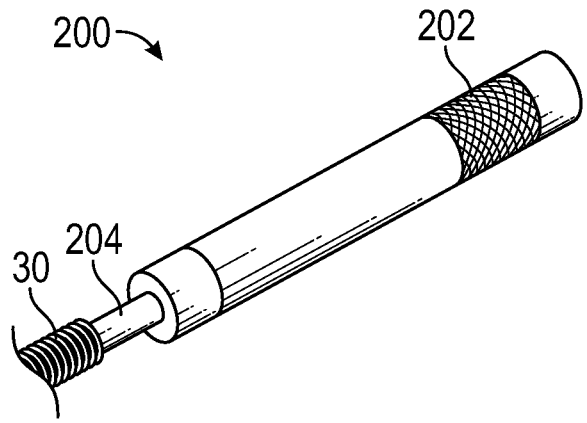
FIG. 4 depicts a perspective view of an alternative embodiment of the ultraviolent air irradiation unit.

Referring now to FIG. 4, a perspective view of an alternative embodiment of the ultraviolent air irradiation unit is shown and generally designated 200.
Embodiments of ultraviolet air irradiation unit 200 may comprise an inlet 202 at one end and an outlet 204 at the opposite end. Unfiltered air enters the ultraviolet air irradiation unit 200 at inlet 202. The unfiltered air is purified by the ultraviolet air irradiation unit 200 by undergoing an irradiation process, along with an optional filtering process. The purified air exits the ultraviolet air irradiation unit 200 at the outlet 204 and enters the breathing tube 30, similar to that depicted in FIG. 1. The purified air is delivered through the breathing tube 30 to a face mask 20, similar to that depicted in FIG. 1 for inhalation by the user. The face mask 20 and the breathing tube 30 may be sterile and air tight, further limiting contamination of the purified air exiting the ultraviolet air irradiation unit 200. Utilizing a sterile face mask 20 and breathing tube 30 further ensures that the wearer is protected from the contaminated environment.

Figure 5:
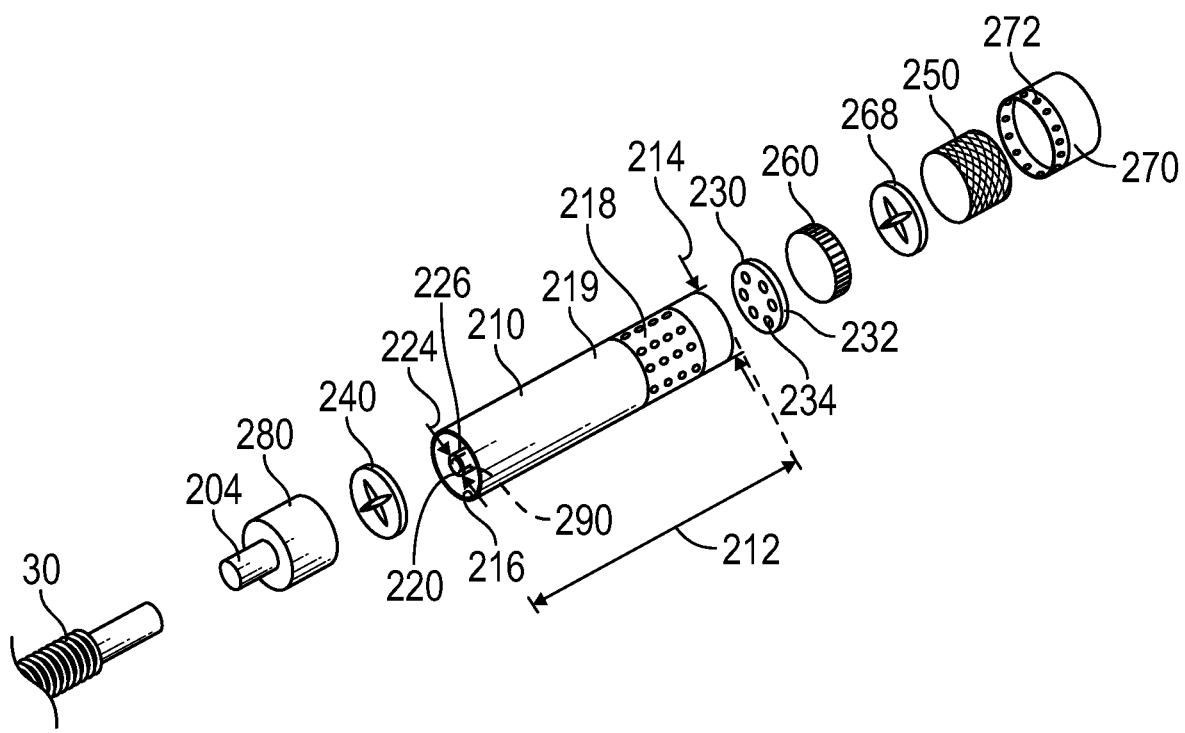
FIG. 5 depicts an exploded view of the alternative embodiment of the ultraviolet air irradiation unit of FIG. 4.

Referring now to FIG. 5, an exploded view of the alternative embodiment of the ultraviolet air irradiation unit 200 is depicted. The ultraviolet air irradiation unit 200 may comprise a chamber 210, internal storage compartment 220, a UV LED apparatus 230, a pressure differential apparatus such as system fan 240, a HEPA filter element 250, a thermal dissipater 260, a thermal dissipater fan 268, a first end cap 270, and a second end cap 280. Embodiments of the ultraviolet air irradiation unit 200 may fit the filtering and irradiating components into a compact, lightweight, and portable unit. In some embodiments of the ultraviolet air irradiation unit 200, the ultraviolet air irradiation unit 200 may be tubular shaped. Embodiments of the invention may be configured to allow the user to easily carry the ultraviolet air irradiation unit 200 in the hand, in a pocket, with a sling to carry over the shoulder, or for placement item into a conventional cup holder in a vehicle.

In the ultraviolet air irradiation unit 200, the chamber 210 is a tube with a length 212 and a diameter 214. The internal wall 216 of the chamber 210 comprises a reflective material, such as a reflective coating, capable of reflecting ultraviolet radiation in the wavelengths of 100-400 nm, such as aluminum. The chamber 210 may be formed with a plurality of air inlet holes 218 and a retaining lip 219 adjacent to the air inlet holes 218. Within the chamber 210, an internal storage compartment 220 may be configured to store a power source 290. The internal storage compartment 220 may be configured as a tube having a length and a diameter 224. The length of the internal storage compartment 220 may be equal to the length 212 of the chamber 210. The external wall 226 of the internal storage compartment 220 may comprise a reflective material, such as a coating, capable of reflecting ultraviolet radiation in the wavelengths of 100-400 nm, such as aluminum. The reflective material of the compartment 210 and the internal storage compartment 220 may be the same to provide for even reflective properties along the length of the ultraviolet air irradiation unit 200.

Due to the reflective materials utilized for the surfaces of the chamber 210 and the internal storage compartment 220, waves of ultraviolet radiation occurring in the void between the chamber 210 and the internal storage compartment 220 will bounce between the reflective surfaces. By utilizing a tube for the chamber 210, a smooth continuous reflective surface may be provided to enhance the even reflection of the UV radiation and directed the UV radiation towards the axial center of the chamber 210 where the internal storage compartment 220 may be located. By utilizing a tube for the storage compartment 220, a smooth continuous reflective surface is provided which enhances the even reflection of the UV radiation and directs the UV radiation outwards back towards the interior wall 216 of the chamber 210. The utilization of tubes and interior surfaces comprising a coatings comprising a UV reflective material enhances the optimal distribution of UV radiation.

One end of the chamber 210 may comprise a UV LED apparatus 230. The UV LED apparatus 230 may have a circular base 232, multiple UV LEDs 234, and electronic controls required to operate the UV LEDs 234. The circular base 232 of the UV LED apparatus 230 is configured to form a seal between the chamber 210 and the UV LED apparatus 230 to prevent air from entering through the end of the chamber 210. An optional HEPA filter element sleeve 250 may be configured to fit around the chamber 210 and over the air inlet holes 218. A thermal dissipater 260 may be disposed adjacent to the UV LED apparatus 230 and is similarly shaped. The thermal dissipater 260 is thermally coupled to the UV LED apparatus 230 and its components. A thermal dissipater fan 268 may be disposed adjacent to and in communication with the thermal dissipater 260. The first end cap 270 includes air inlet holes 272 and air outlet holes 274 (shown in FIG. 6). The first end cap 270 may be configured to house the UV LED apparatus 230, the thermal dissipater 260, and the thermal dissipater fan 268. The thermal dissipater fan 268 pulls air in through the air inlet holes 272 and through the thermal dissipater 260 to remove heat from the thermal dissipater 260, which in turns removes heat from the UV LED apparatus 230. The heat is exhausted through the air outlet holes 274. The thermal dissipater 260 minimizes the heat load imparted by the UV LEDS 234 on air passed through chamber 210.

The first end cap 270 encloses the end of the chamber 210 and, if utilized, presses an optional HEPA filter element sleeve 250 between the retaining lip 219 and the first end cap 270. The optional HEPA filter element sleeve 250 has a high MERV. The HEPA filter element sleeve 250 is not restricted to a single type of filter and may be interchangeable to meet certain requirements, such as a 95%-100% filter rating, for use in environments with oil. Once the HEPA filter element sleeve 250 is saturated, it may be replaced with a new unused HEPA filter element sleeve 250. The UV LEDs apparatus 230 may be configured to form a seal with the chamber 210 to control and direct the air into the ultraviolet air irradiation unit 200 only through the air inlet 218, which directs air entering the ultraviolet air irradiation unit 200 to be filtered by the HEPA filter element sleeve 250.

The opposite end of the chamber 210 may comprise a pressure differential apparatus such as system fan 240. The system fan 240 provides the required pressure differential for directing air flow through the system. The system fan 240 provides the pressure differential which drives air flow through the system. System fan 240 may be configured to provide variable air flow rates. The second end cap 280 may be formed with the air outlet 204 and configured to enclose the second end of the chamber 210. The second end cap 280 may form a seal with the exterior of the chamber 210 to control and direct the air out of the ultraviolet air irradiation unit 200 only through the air outlet 204. This feature enhances the flow of air exiting the ultraviolet air irradiation unit 200 into the breathing tube 30. A power source 290 disposed within internal compartment storage 220 may be used to power some or all of the electronic components of the invention.

Embodiments of the ultraviolet air irradiation unit 200 may purify air of air particulates, gases, vapors, and biological material by utilizing a combination of an optional HEPA filter element sleeve 250 with a high MERV and by utilizing the UV LEDs 234, which emit light in the germicidal wavelengths of 100-280 nm. In these embodiments, the ultraviolet air irradiation unit 200 first filters air of air particulates, gases, vapors, and biological material by passing air through the HEPA filter element sleeve 250. The ultraviolet air irradiation unit 200 thereafter irradiates the air to neutralize biological material, such as fungi, viruses, and bacteria by utilizing UV LEDs typically operating in the germicidal wavelengths of 100-280 nm.

Embodiments of the ultraviolet air irradiation unit 200 may be powered by an internal rechargeable battery pack 290 which may be utilized to provide power to the ultraviolet air irradiation unit 200. A pressure differential apparatus, such as a system fan 240, pulls air through the HEPA filter element sleeve 250 through the air inlet holes 218, which filters and reduces the number of harmful particulates entering the unit. The filtered air flows through the chamber 210. The wall of the chamber 210 comprise a reflective material, such as a reflective coating, which bounces the UV radiation between the interior wall 216 of the chamber 210 and the exterior wall 226 of the internal storage compartment 220 to maximize the germicidal effectiveness of the ultraviolet air irradiation unit 200.

The ultraviolet air irradiation unit 200 may be connected to the face mask 10 with the breathing tube 30. Air flow may be allowed to flow only from the ultraviolet air irradiation unit 200 to the face mask 30. The filtered and irradiated air flows through the air outlet 204 of the second end cap 280 by the system fan 240. The filtered and irradiated air flows through the sterile breathing tube 30 and into the sterile face mask 20. The filtered and irradiated air is inhaled by the user and the face mask 20 may exhaust exhalations by the user. The face mask 20 may be sterile, not exposed to the contaminated environment and thereby providing the user with filtered and irradiated air free of air particulates, gases, vapors, and biological material.

In an embodiment of the ultraviolet air irradiation unit 200, the UV LED apparatus 230 may comprise six UV LEDs 234. The UV LEDs 234 are UV-C LEDs and configured to emit UV radiation in the wavelength range of 100-280 nm. In one embodiment of the invention, the six UV-C LEDs 234 may be configured to emit UV radiation in the range of 260-270 nm, with each having an output power of 60 mW. The UV LED apparatus 230 may have the UV LEDs 234 configured in a circle. In this embodiment, the UV LED apparatus 230 fits over the end of the chamber 210 so the placement of the UV LEDs 234 in a circle places the UV LEDs 234 in the void between the chamber 210 and the internal storage compartment 220. The reflective surfaces of the inner walls of chamber 210 and the outer walls of the internal storage compartment 220 may take advantage of the radiation pattern of the UV LEDs 234. In general, the radiation pattern of the UV LEDs 234 is spherical. By positioning the UV LEDs 234 perpendicular to the interior wall 216 of the chamber 210 and the internal storage compartment 220, the UV radiation waves emitted on the sides of the UV LEDs 234 are reflected back towards the center. The total irradiance of the ultraviolet air irradiation unit 200 is approximately 10 mW/cm$^2$ along the length, with 6 seconds of exposure in the ultraviolet air irradiation unit 100 give approximately 60 mJ/cm$^2$, which neutralizes approximately 99.99% of biological material in the incoming air stream.

The purified air, which is irradiated and optionally filtered, then flows through the air outlet 204 and into the breathing tube 30. The purified air is then pushed to the face mask 20 through the breathing tube 30 where the user is able to inhale the purified air. The ultraviolet air irradiation unit 200 may provide positive air pressure to the face mask 20 to provide the user with comfortable breathing and to prevent the backflow of air into the ultraviolet air irradiation unit 200. The differential pressure provided by the ultraviolet air irradiation unit 200, which may be coupled with an exit valve in the face mask 20, facilitates the exhaustion of the user's exhalations from the system. The ultraviolet air irradiation unit 200 may have a variable air flow rate to adapt to the user's need. The ultraviolet air irradiation unit 200 and face mask 20 may also include a reversible function to purify a user's exhalations before purging it from the ultraviolet air irradiation system.

Figure 6:
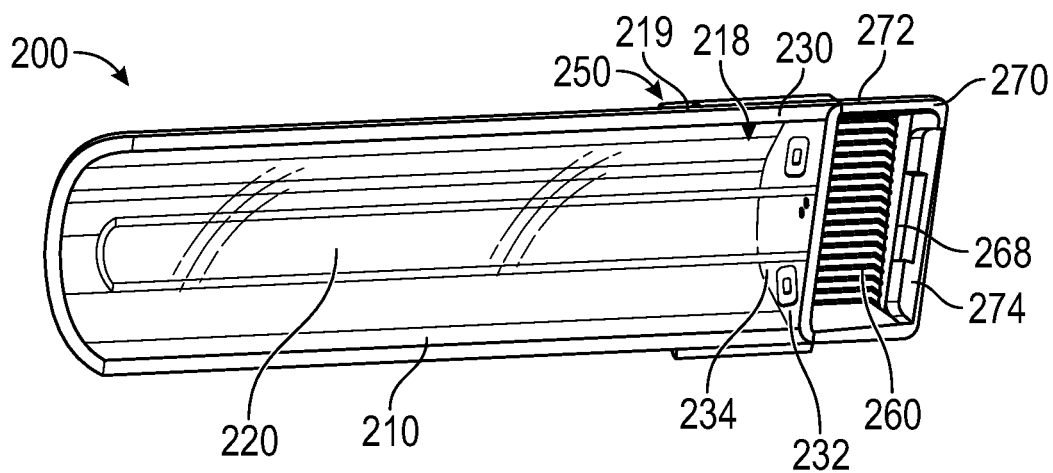
FIG. 6 depicts a sectioned view of an embodiment of the ultraviolet air irradiation unit.

Referring now to FIG. 6, a sectioned view of the ultraviolet air irradiation unit 200 is shown. The UV LED apparatus 230 may comprise a circular base 232 which is configured to form a seal between the chamber 210 and the UV LED apparatus 230 to prevent air from entering through the end of the chamber 210. A HEPA filter element sleeve 250 may be configured to fit around the chamber 210 and over the air inlet holes 218. A thermal dissipater 260 may be disposed adjacent to the UV LED apparatus 230 and may comprise a similar shape. The thermal dissipater 260 may be thermally coupled to the UV LED apparatus 230 and its components. A thermal dissipater fan 268 may be disposed adjacent to and in communication with the thermal dissipater 260. A first end cap 270 includes air inlet holes 272 and air outlet holes 274. The first end cap 270 may be configured to house the UV LED apparatus 230, the thermal dissipater 260, and the thermal dissipater fan 268. The thermal dissipater fan 268 pulls air through the air inlet holes 272 and through the thermal dissipater 260 to remove heat from the thermal dissipater 260, which in turns removes heat from the UV LED apparatus 230. The heat is exhausted through the air out holes 274. The first end cap 270 encloses the end of the chamber 210 and is configured to press an optional HEPA filter element sleeve 250 between the retaining lip 219 and the first end cap 270.

Figure 7:
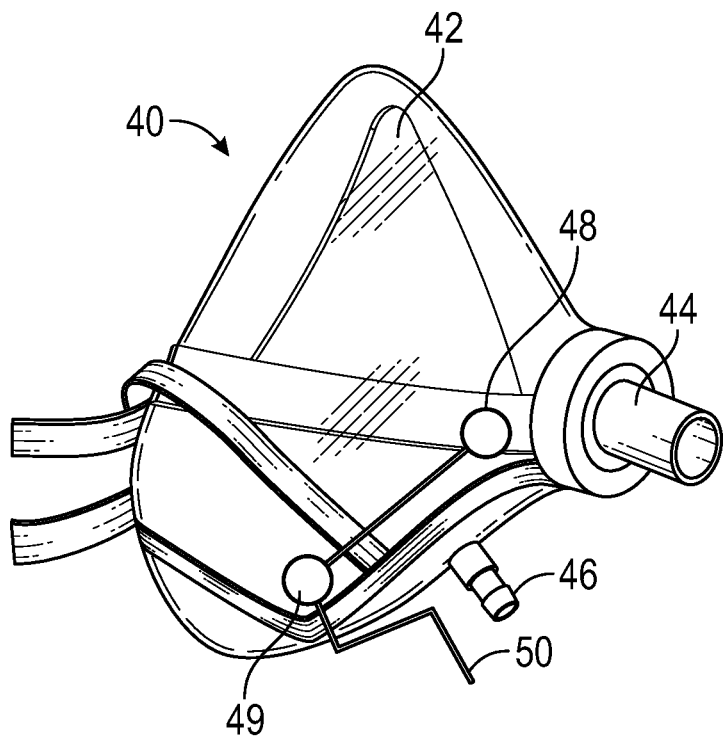
FIG. 7 depicts a perspective view of an alternative embodiment of the face mask of the present invention.

Referring now to FIG. 7, an alternative embodiment of a face mask of the present invention is shown and generally designated 40. The face mask 40 includes a mask body 42 configured to seal to the face of a user. The mask body 42 includes an air inlet 46 for the purified air to enter and an air outlet valve 44 to exit the mask body 42. An oxygen sensor 49 may be disposed adjacent the air inlet 46 and the surface of the mask body 42. A carbon dioxide sensor 48 may be disposed adjacent the air outlet valve 44. The oxygen sensor 49 and carbon dioxide sensor 48 may include a communication link 50 which is configured to provide communications with the ultraviolet air irradiation unit 100, which unit 100 may be configured to communicate with the oxygen sensor 49 and carbon dioxide sensor 44 of the face mask 40. The oxygen sensor 49 and carbon dioxide sensor 48 works in conjunction to monitor the levels of oxygen and carbon dioxide present in the face mask 40. This configuration enhances the ability of the ultraviolet air irradiation system 10 to provide the user with an acceptable amount of oxygen while also facilitating the ability of the ultraviolet air irradiation system 10 to exhaust the proper amount of carbon dioxide.

In an embodiment of the ultraviolet air irradiation system 10 utilizing the face mask 40, the ultraviolet air irradiation unit 100, 200 may work in conjunction with the face mask 40 to monitor the levels of oxygen and carbon dioxide present in the face mask 40. When the oxygen level is too low as measured by the oxygen sensor 49 or the carbon dioxide level is too high as measured by the carbon dioxide sensor 48, the air flow rate from the ultraviolet air irradiation unit 100 or ultraviolet air irradiation unit 200 may be increased to correct the respective levels. The increase in air flow rate, and differential pressure, will cause additional oxygen to flow into the face mask 40 and exhaust the carbon dioxide through the outlet valve 44. This configuration provides the the user with acceptable oxygen intake levels while exhausting carbon dioxide from the system.

Figure 8:
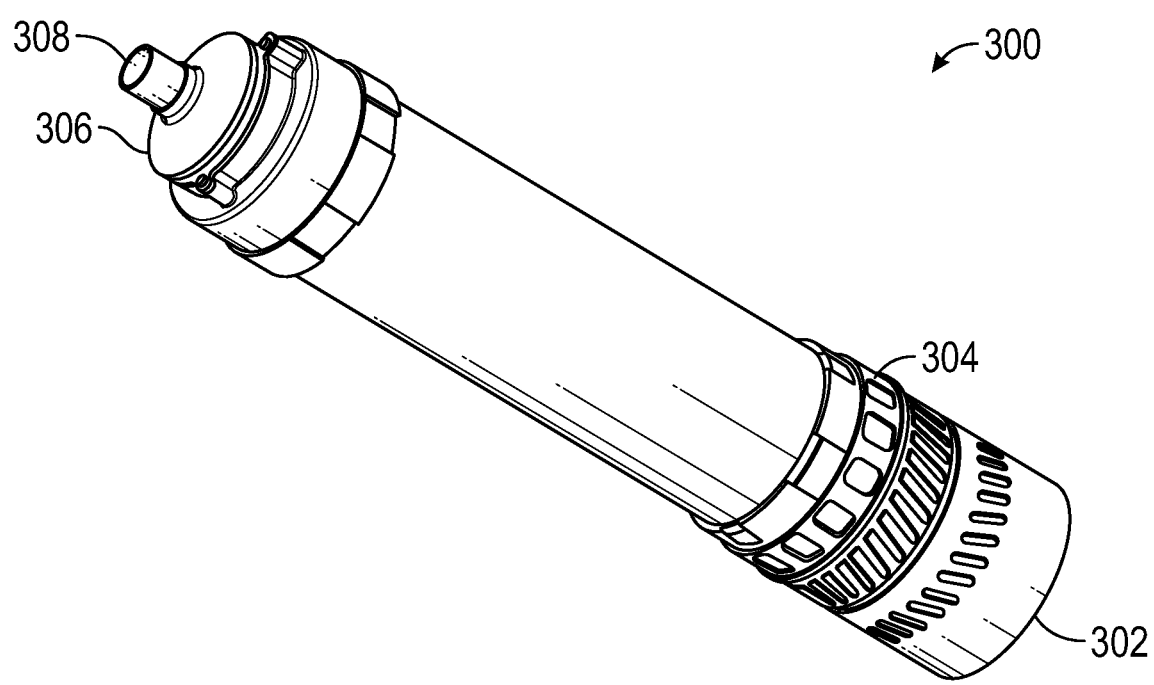
FIG. 8 depicts a perspective view of an alternative embodiment of the ultraviolet air irradiation unit of the present invention.

Referring now to FIG. 8, a perspective view of an alternative embodiment of the ultraviolent air irradiation unit is shown and generally designated 300. As shown, the ultraviolet air irradiation unit 300 includes a first end 302 with an air inlet 304 located towards the first end 302 and a second end 306 with an air outlet 308 located at the tip of the second end 306. Unfiltered air enters the ultraviolet air irradiation unit 300 at air inlet 304. The unfiltered air is irradiated by the ultraviolet air irradiation unit 300 by undergoing an irradiation process. The irradiated air exits the ultraviolet air irradiation unit 300 at the air outlet 308 and enters the breathing tube 30 (shown in FIG. 1). The irradiated air flow through the breathing tube 30 to the face mask 20 (shown in FIG. 1) for inhalation by the user. The face mask 20 and the breathing tube 30 may be sterile and airtight, which prevents contamination of the irradiated air exiting the ultraviolet air irradiation unit 300.

Figure 9:
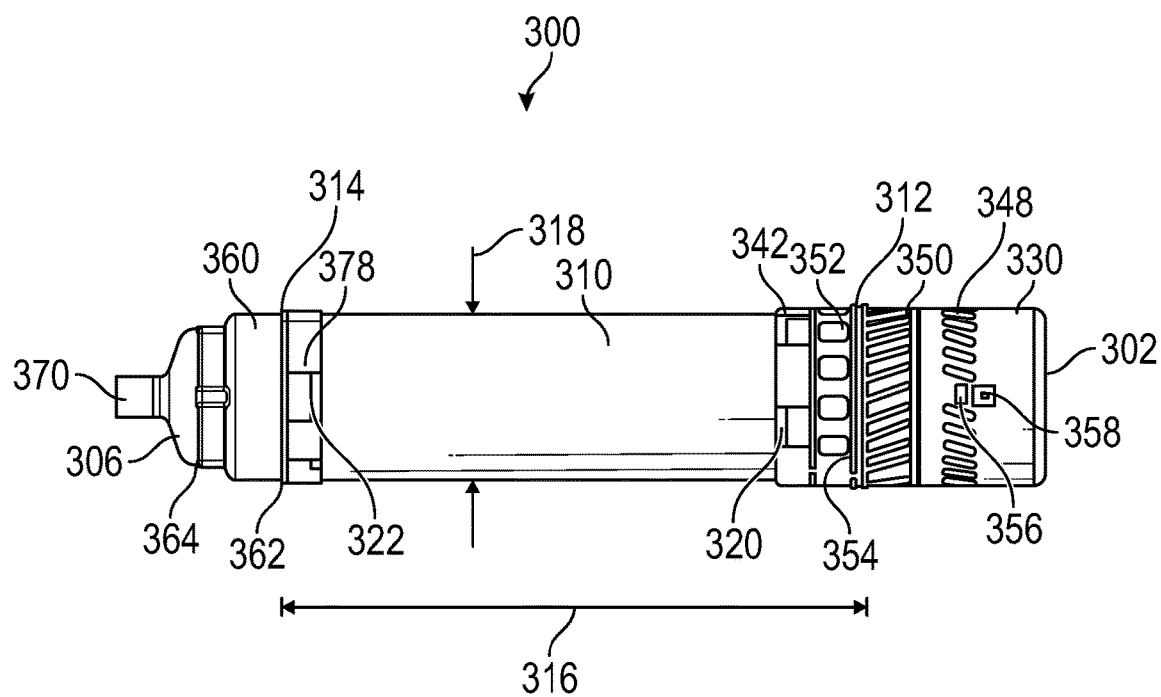
FIG. 9 depicts a first side view of the alternative embodiment of the ultraviolet air irradiation unit shown in FIG. 8.

Referring now to FIG. 9, a first side view of an embodiment of an ultraviolet air irradiation unit 300 is shown. The ultraviolet air irradiation unit 300 includes a body 310 with a first end 312 and a second end 314. The body 310 has a length 316 and an exterior diameter 318. A first circumferential groove may be disposed towards the first end 312 of the body 310. A second circumferential groove 322 may be disposed towards the second end 314 of the body 310. The body 310 of the ultraviolet air irradiation unit 300 may be tubular with length 316 and exterior diameter 318.

A first end cap 330 may be removably attached to the first end 312 of the body 310 and a second end cap 360 may be removably attached to the second end 314 of the body 310. The first end cap 330 may include a heat dissipater outtake 348, a heat dissipater intake 350, an air intake 352, HEPA filter retainer rings 354, a power switch 356, a charging port 358, and/or a plurality of tabs 342. The second end cap 360 may include a plurality of tabs 378 extending from a first open end 362 and/or an air outlet nipple 370 extending from a second open end 364. The plurality of tabs 342 may be configured to fit around the body 310 and snap into the first circumferential groove 320 of the body 310 to secure the first end cap 330 to the body 310. Likewise, the plurality of tabs 378 may be configured to fit around the body 310 and snap into the second circumferential groove 322 of the body 310 to secure the second end cap 360 to the body 310.

Figure 10:
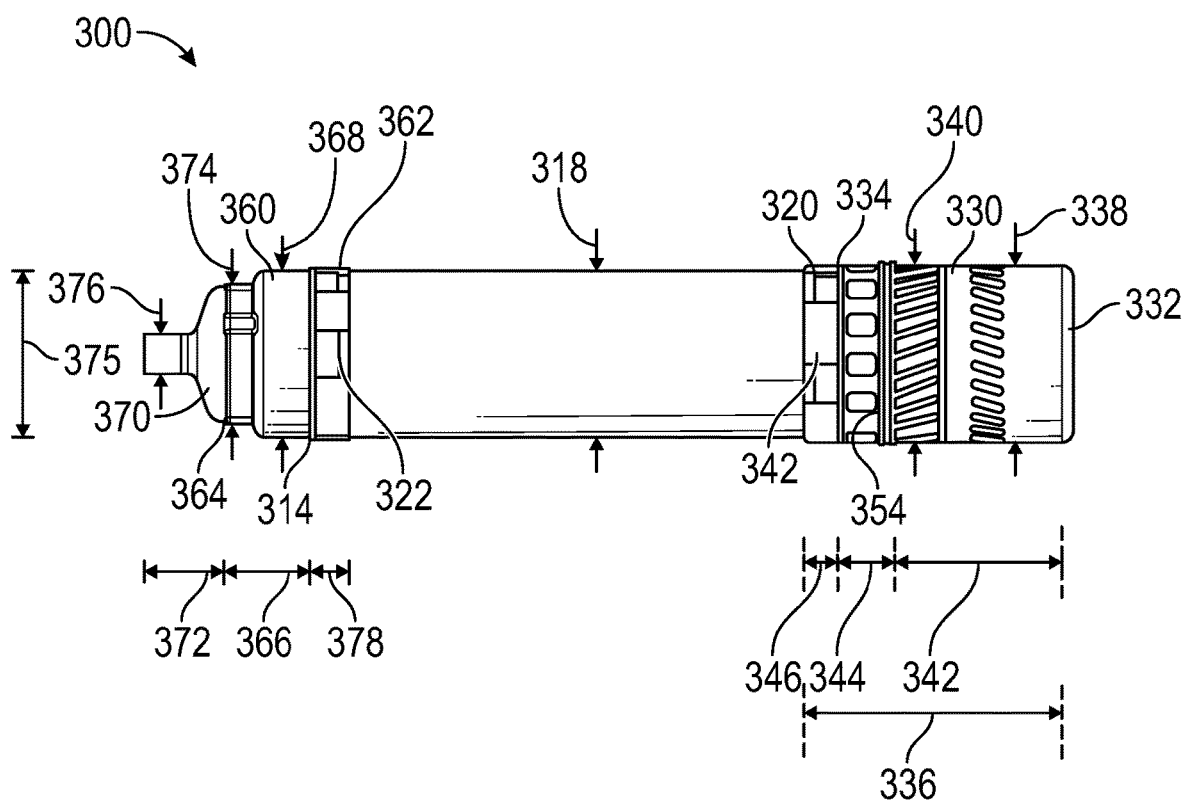
FIG. 10 depicts a second side view of the alternative embodiment of the ultraviolet air irradiation unit shown in FIG. 8.

Referring now to FIG. 10, a second side view of an embodiment of an ultraviolet air irradiation unit 300 is shown. The first end cap 330 may be formed with a closed end 332 and an open end 334. The first end cap 330 has an overall length 336 between the closed end 332 and the open end 334 with a first exterior diameter 338 along length 342 of the first end cap 330 that may transition to a second diameter 340 along the remaining length 344. The first diameter 338 may be approximately equal to the exterior diameter 318 of the body 310 and the second diameter 340 may be larger than the exterior diameter 318 of the body 310. This configuration allows the portion of the first end cap 330 with diameter 340 to fit over the body 310 with the portion of the first end cap 330 with the smaller first diameter 338 abutting against the first end 312 of the body 310. Extending from the open end 334 of the first end cap 330 is the plurality of tabs 342 with length 346, which are configured to fit around the body 310 and snap into the first circumferential groove 320 of the body 310 to secure the first end cap 330 to the body 310.

The second end cap 360 has a length 366 and a diameter 368 approximately equal to the exterior diameter 318 of the body 310 which may narrow to diameter 374. Extending from the first open end 362 of the second end cap 360 may be disposed a plurality of tabs 378 with length 378, which fit around the body 310 and snap into the second circumferential groove 322 of the body 310 to secure the second end cap 360 to the body 310. This configuration allows the first open end 362 of the second end cap 360 to abut against the second end 314 of the body 310. An air outlet nipple 370 may extend from the second open end 364 of the second end cap 360. The air outlet nipple 370 may have a length 372 which may have an inlet diameter 375 which narrows to an outlet diameter 376.

Figure 11:
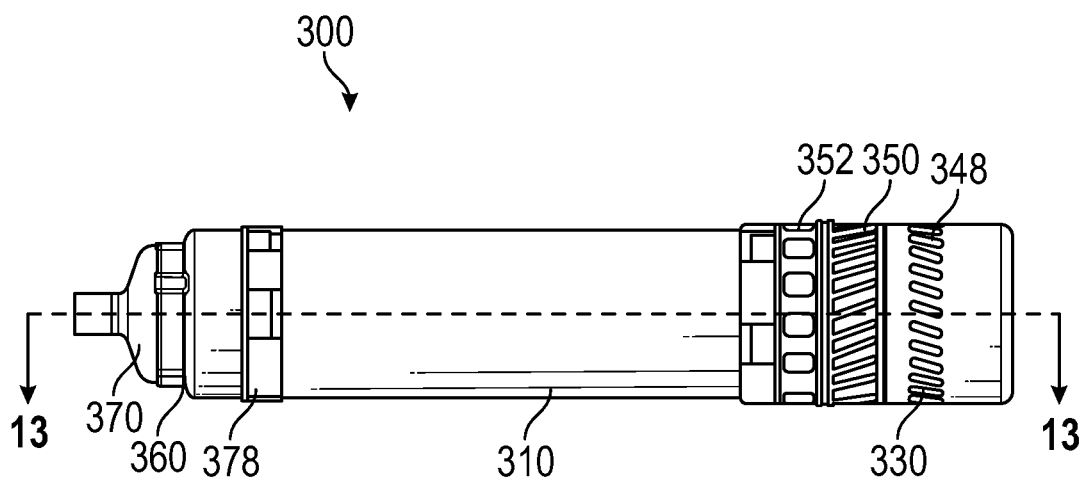
FIG. 11 depicts a third side view of the alternative embodiment of the ultraviolet air irradiation unit shown in FIG. 8.

Referring now to FIG. 11, a third side view of an embodiment of an ultraviolet air irradiation unit 300 is shown. The ultraviolet air irradiation unit 300, the body 310, the first end cap 330, and the second end cap 360 may be configured to have a cylindrical tube shape. As a result, the ultraviolet air irradiation unit 300 is substantially similar on all sides. Heat dissipater outtake 348, heat dissipater intake 350, air intake 352, filter retainer rings 354, and tabs 342 of the first end cap 330 may be configured to have substantially similar diameters along the circumference of the first end cap 330. Similarly, the air outlet nipple 370 and tabs 378 may be configured to have a substantially similar diameter along the circumference of the second end cap 360.

Figure 12:
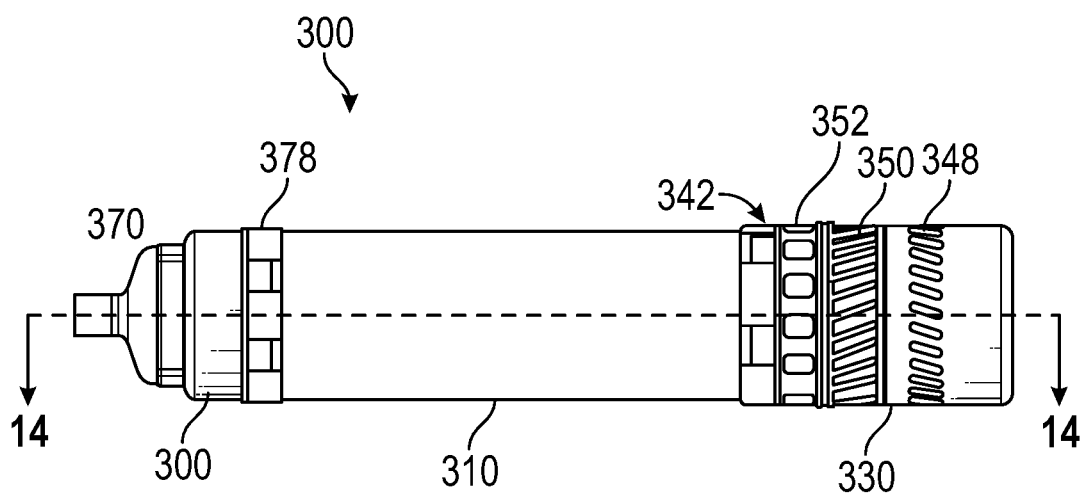
FIG. 12 depicts a fourth side view of the alternative embodiment of the ultraviolet air irradiation unit shown in FIG. 8.

Referring now to FIG. 12, a fourth side view of an embodiment of an ultraviolet air irradiation unit 300 is shown. Heat dissipater outtake 348, heat dissipater intake 350, air intake 352, filter retainer rings 354, and tabs 342 of the first end cap 330 may be configured to have substantially similar diameters along the circumference of the first end cap 330.

Figure 13:
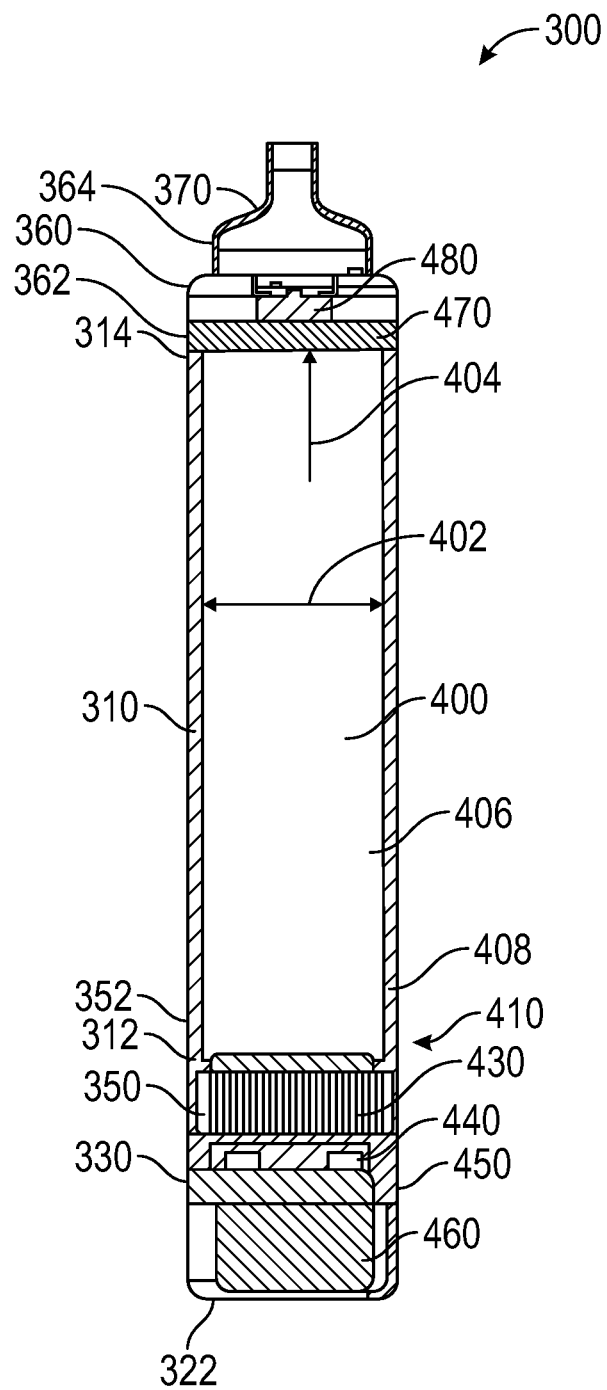
FIG. 13 depicts a sectioned view along line 13-13 in FIG. 11.

Referring now to FIG. 13, a cross-section of an embodiment of an ultraviolet air irradiation unit 300 taken along line 13-13 in FIG. 11 is shown. Located within the body 310 is an irradiation chamber 400. The irradiation chamber 400 has an internal diameter 402 and a length 404 equal to the length 316 of the body 310 as shown in FIG. 9. The irradiation chamber 400 comprises an ultraviolet reflective material 406 on its inside surface capable of reflecting ultraviolet radiation in the wavelengths of 100-400 nm, such as aluminum. To enhance the maximum reflective properties of the ultraviolet reflective material 406, the inside surface may be smooth and without surface irregularities. Body 310 is configured to have internal air intake 408 which may be aligned with air intake 352 of the first end cap 330. Irradiation chamber 400 may be configured to comprise the interior of the body 310 to decrease manufacturing complexity and increase cost efficiency.

First end cap 330 may be configured to house a UV LED apparatus 410, a thermal dissipater 430, a thermal dissipater fan 440, an electronic control module 450, and/or a battery pack 460. The UV LED apparatus 410 may be located at an expansion joint between the first diameter 338 and the second diameter 340 of the first end cap 330 as shown in FIG. 10. The thermal dissipater 430 may be located adjacent to the heat dissipater intake 350 and the thermal dissipater fan 440 may be adjacent to the heat dissipater outtake 348. The electronic control module 450 and the battery pack 460 may be located adjacent to the closed end 332. Second end cap 360 may be configured to house a reflection apparatus 470 and a system fan 480. The reflection apparatus 470 may be adjacent to the first open end 362 and system fan 480 may be adjacent to the second open end 364 towards the air outlet nipple 370.

Figure 14:
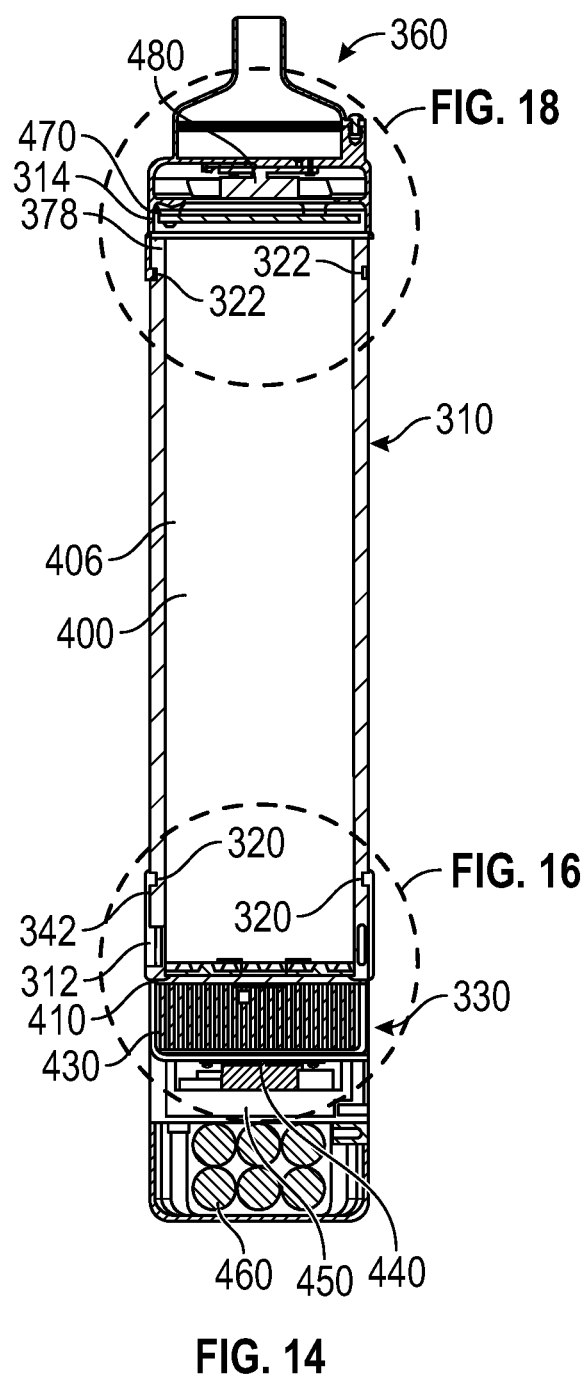
FIG. 14 depicts a sectioned view along line 14-14 from FIG. 12 and showing the location of detailed views within circles referencing FIGS. 16 and 18.

Referring now to FIG. 14, a cross-section of an embodiment of an ultraviolet air irradiation unit 300 taken along line 14-14 in FIG. 12 is shown. The body 310 of the ultraviolet radiation unit 300 houses the irradiation chamber 400. A first end cap 330, which encloses the first end 312 of the body 310, may be configured to house a UV LED apparatus 410, a thermal dissipater 430, a thermal dissipater fan 440, a electronic control module 450, and/or the battery pack 460. The UV LED apparatus 410 may be partially inserted within the irradiation chamber 400. The second end cap 360, configured to house the reflection apparatus 470 and/or the system fan 480, encloses the second end 314 of the body 310. The reflection apparatus 470 may be located outside of, and overlapping, the opening of the irradiation chamber 400.

Due to the reflective surface provided by the ultraviolet reflective material 406 of the irradiation chamber 400, the ultraviolet radiation provided by the UV LED apparatus 410 will bounce between the reflective surfaces. By utilizing the interior surface of the cylindrical tube for the irradiation chamber 400, a smooth continuous reflective surface may be provided so that UV radiation is evenly reflected and dead spots which may otherwise caused by irregular surface patterns, such as sharps corners in square tubes, are minimized or eliminated. The reflection apparatus 470 may overlap the opening of the irradiation chamber 400 with a reflective surface to reflect any UV radiation directed out of the irradiation chamber 400 back into the irradiation chamber 400. The reflective surface of the irradiation chamber 400 directs the UV radiation towards an opposing reflective surface, which in turn reflects the UV radiation towards another opposing reflective surface, and so on. This configuration multiplies the exposure of a single particulate to UV radiation within the irradiation chamber 400 thereby increasing the efficacy of the irradiation chamber 400 to eliminate any biological material.

The tabs 342 of the first end cap 330 may fit over the body 310 and snap into the first circumferential groove 320 of the body and the tabs 378 of the second end cap 360 may fit over the body 310 and snap into the second circumferential groove 322 to enclose the body 310, and the irradiation chamber 400, between the first end cap 330 and the second end cap 360. Removing the first end cap 330 from the body 310 involves separating the tabs 342 from the first circumferential groove 320 and pulling the first end cap 330 away from the body 310. Removing the first end cap 330 removes, if first end cap 330 is so configured, the UV LED apparatus 410, the thermal dissipater 430, the thermal dissipater fan 440, the electronic control module 450, and/or the battery pack 460 from the body 310. Similarly, removing the second end cap 360 from the body 310 involves separating the tabs 378 from the second circumferential groove 322 and pulling the second end cap 360 away from the body 310. Removing the second end cap 360, if second end cap 360 is so configured, removes the reflection apparatus 470 and/or the system fan 480 from the body 310. Locating the components in the first end cap 330 and the second end cap 360 provides quick access to the various components for repair or replacement. The removal of the first end cap 330 and the second end cap 360 also provides access to the irradiation chamber 400 for cleaning or for inspection.

Figure 15:
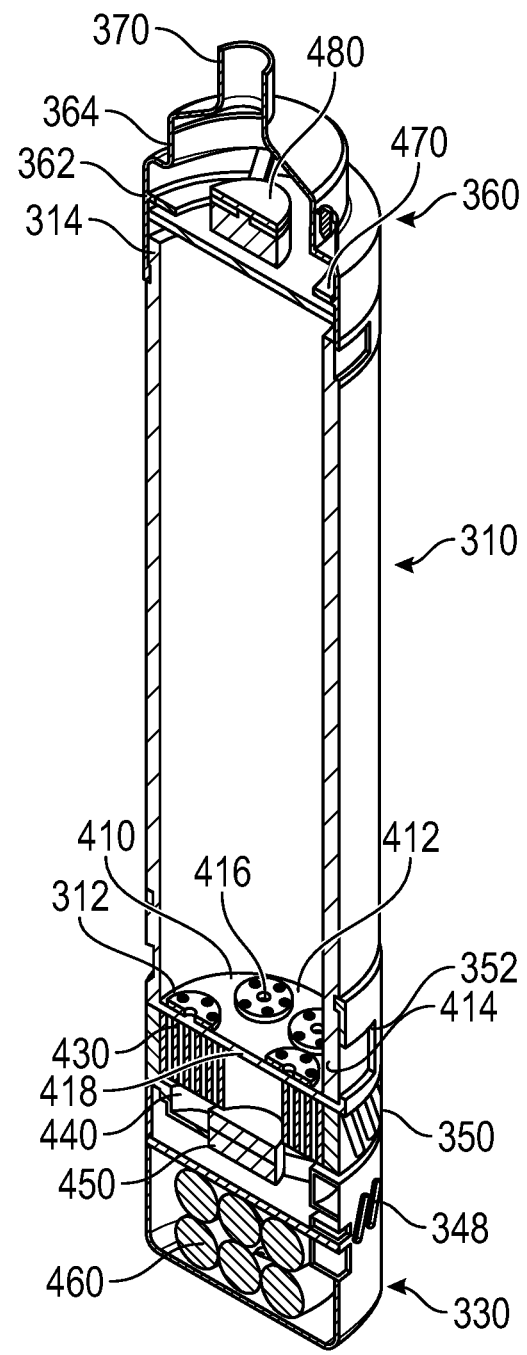
FIG. 15 shows a perspective view of the sectioned view depicted in FIG. 14.

Referring now to FIG. 15, a perspective view of a cross-section of an embodiment of an ultraviolet air irradiation unit 300 as depicted in FIG. 14 is shown. The first end cap 330 may be configured to house the UV LED apparatus 410, the thermal dissipater 430, the thermal dissipater fan 440, the electronic control module 450, and/or the battery pack 460. First end cap 330 encloses the first open end 312 of the body 310. The UV LED apparatus 410 may have a circular base 412. An annular groove 414 may be formed into the perimeter of the circular base 412. Multiple UV LEDs 416 may be disposed on the top surface of the circular base 412 and the electronic controls 418 to operate the UV LEDs 416 may be located on the bottom surface of the circular base 412. The circular base 412 of the UV LED apparatus 410 may be configured to form a seal in the first end cap 330 at an expansion joint between the first diameter 338 and the second diameter 340, shown in FIG. 10, to prevent air from the heat dissipater intake 350 from entering the irradiation chamber 400. This seal is provided to prevent air entry into irradiation chamber 400 except through the air intake 352.

A thermal dissipater 430 may be disposed opposite and adjacent to the UV LED apparatus 410. The thermal dissipater 430 is thermally coupled to the UV LED apparatus 410 and its components and serves as a heat sink to soak up heat produced by the UV LED apparatus 410. The thermal dissipater fan 440 may be adjacent to and in communication with the thermal dissipater 430. The thermal dissipater fan 440 pulls air in through the heat dissipater intake 350 and through the thermal dissipater 430 to remove heat from the thermal dissipater 430, which in turns removes heat from the UV LED apparatus 410. The heat is exhausted through the heat dissipater outtake 348. The thermal dissipater 430, used in conjunction with the thermal dissipater fan 440, may be used to regulate the temperature of the UV LED apparatus 410 at operating temperatures. Additionally, since the UV LED apparatus 410 is the primary heat producing component of the ultraviolet air irradiation unit 300, by regulating the temperature of the UV LED apparatus 410 the overall temperature of the ultraviolet air irradiation unit 300 may be regulated to proper handling temperatures.

An electronic control module 450 and/or an internal rechargeable battery pack 460 may be disposed adjacent to the thermal dissipater fan 440. The electronic control module 450 may provide electronic control for the ultraviolet air irradiation unit 300 and may be in communication with a pressure differential apparatus, such as system fan 480, the UV LED apparatus 410, the thermal dissipater fan 440, and/or the battery pack 460. The electronic control module 450 may vary the air flow rate of the system to compensate for the user's intake of air, increase the cooling effects of the thermal dissipater 430, and regulate power delivery to various components. The electronic control module 450 may also be expandable to include additional controls, such as receiving digital imput provided by the oxygen and carbon dioxide sensors and reacting to the readings. The ultraviolet air irradiation unit 300 may be powered by the internal rechargeable battery pack 460 which may be charged via power connector 358, shown in FIG. 9, via USB. In addition, or alternatively, the unit can also be charged via a shirt containing solar panels for convenient on-the-go power.

A HEPA filter may be used with the ultraviolet air irradiation unit 300 if desired. If utilized, a HEPA filter will be substantially similar to the HEPA filter element sleeve 250 described above. The HEPA filter element sleeve 250 may be configured to attach to the HEPA filter retainer rings 354, with the HEPA filter element sleeve 250 configured will fit over the air intake 352 of the first end cap 330. The HEPA filter will filter the air entering the ultraviolet air irradiation unit 300. In situations where a HEPA filter is not needed, the air intake 352 is free of an obstruction and enables unobstructed air to flow into the irradiation chamber 400.

On the opposite end of the irradiation chamber 400 may be disposed the reflection apparatus 470 and/or pressure differential device, such as system fan 480. The reflection apparatus 470 may overlap the opening of the irradiation chamber 400 with a reflective surface to reflect any UV radiation directed out of the irradiation chamber 400. The pressure differential device, such as system fan 480, provides adequate air flow required for the system and may have the capability of variable air flow rates and/or reversing the direction of the flow through the system. The second end cap 360 is formed with the first open end 362 and is configured to enclose the second end of the irradiation chamber 400. The first open end 362 of the second end cap 360 forms a seal with the second open end 314 of the body 310 to control and direct the air out of the ultraviolet air irradiation unit 300 through the second open end 364 of the second end cap and through air outlet nipple 370 and thereafter to breathing tube 30.

It is to be appreciated by those skilled in the art that the pressure differential apparatus, such as system fan 480, can reverse the flow of air through the system such that the air exhaled from a user could be captured by an alternative mask with a reversed one way valve which would enable a user to inhale air directly into the alternative mask. The mask would then capture the user's exhaled air and direct the same into the breathing tube 30 and into the irradiation chamber 400 for treatment. Then, ultimately the treated air exit the system at the air intake 352. Such a reversal configuration could be useful in treating exhaled air from a sick patient to protect first responders and treating medical personnel.

Figure 16:
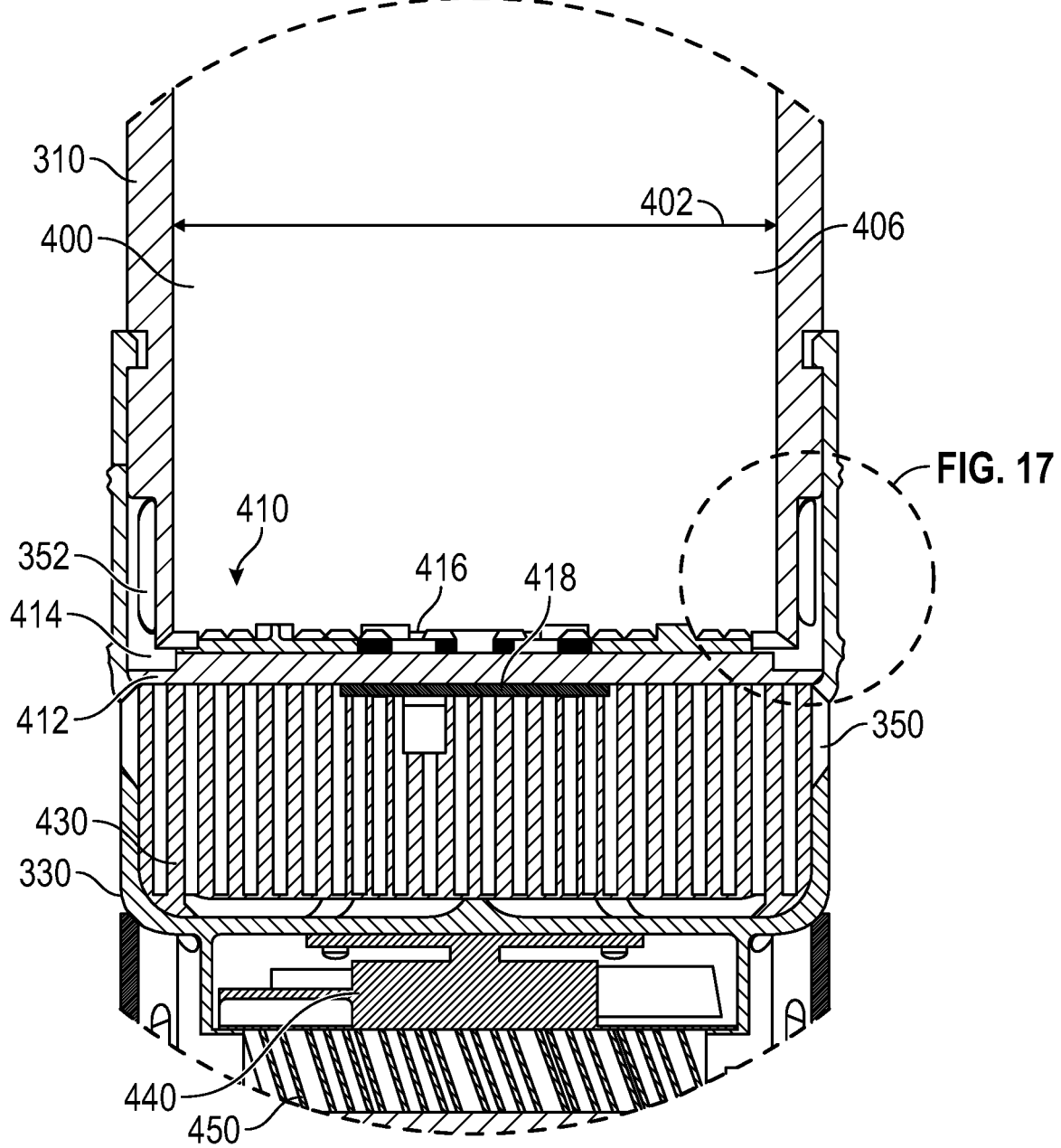
FIG. 16 is a close-up view of the referenced circled portion of FIG. 14, FIG. 16 also showing the location of a detailed view referencing FIG. 17.

Referring now to FIG. 16, a detailed view of portion 16 of the cross-section shown in FIG. 14 is depicted. The UV LED apparatus 410 may include circular base 412 having an annular groove 414 formed into the perimeter of the circular base 412. Multiple UV LEDs 416 may be disposed on the top surface of the circular base 412. Electronic controls for operating the UV LEDs 416 may be disposed on the bottom surface of the circular base 412. The circular base 412 of the UV LED apparatus 410 may be configured to form a seal in the first end cap 330 at the expansion joint between the first diameter 338 and the second diameter 340, shown in FIG. 10, to reduce or prevent air from the heat dissipater intake 350 from entering the irradiation chamber 400 and thus limiting air entry into the irradiation chamber 400 to the air intake 352.

The UV LED apparatus 410 shown in FIG. 16 may include six UV LEDs 416. The UV LEDs 416 are UV-C LEDs and will typically emit UV radiation in the wavelength range of 100-280 nm. More specifically, the six UV-C LEDs 416 may emit UV radiation in the range of 260-270 nm, with each having an output power of 60 mW. The UV LED apparatus 410 may have the UV LEDs 416 configured within a circle having a diameter smaller than the diameter 402 of the irradiation chamber 400. The UV LED apparatus 410 may be configured to fit over one end of the irradiation chamber 400 thereby placing the UV LEDs 416 in the irradiation chamber 400 and with the circular base 412 located on the outside of the irradiation chamber 400. The reflective surfaces of the irradiation chamber 400 and the reflection apparatus 470 may take advantage of the radiation pattern of the UV LEDs 416 in the UV LED apparatus 410. By positioning the UV LEDs 416 of the UV LED apparatus 410 perpendicular to the reflective material 406 comprising the interior surfaces of the irradiation chamber 400, the UV radiation emitted is reflected between the reflective material of the chamber. By positioning the reflection apparatus 470 opposite of the UV LEDs 416 of the UV LED apparatus 410, as shown in FIG. 14, the UV radiation emitted straight out of the UV LEDs 416 of the UV LED apparatus 410 is reflected back into the chamber. The UV radiation of the UV LEDs 416 are thus reflected multiple times to increase the efficacy of the irradiation chamber 400

Figure 17:
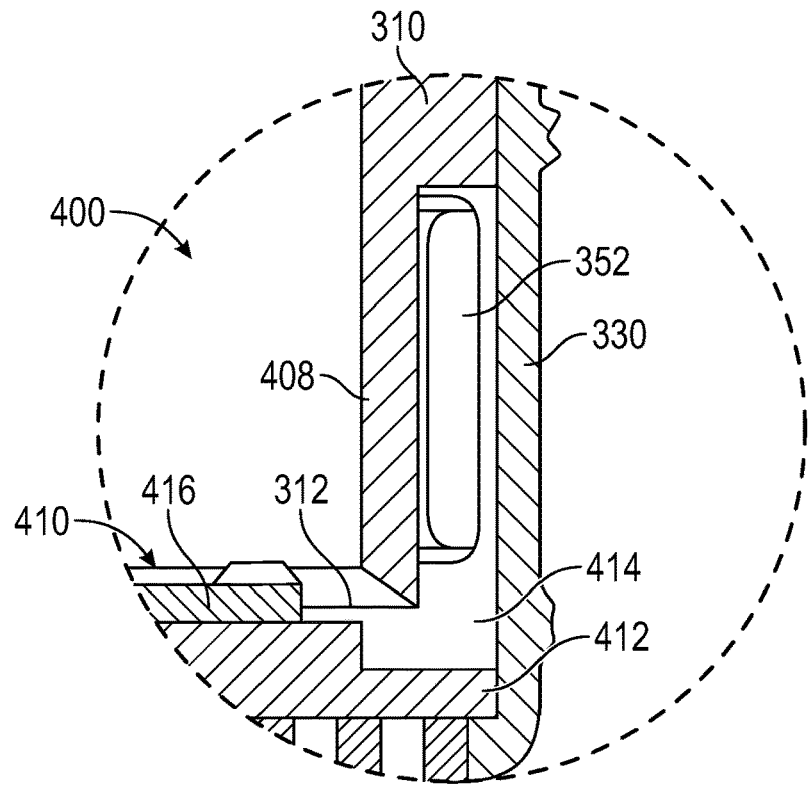
FIG. 17 is a close-up view of the referenced circled portion of FIG. 16.

Referring now to FIG. 17, a detailed view of portion 17 from FIG. 16 is depicted. The first end cap 330 attaches to the first end 312 of the body 310 and may orient the UV LED apparatus 410 in position with respect to the open end of the irradiation chamber 400. The circular base 412 of the UV LED apparatus 410 may be configured to form a seal in the first end cap 330 to prevent air from the heat dissipater intake 350 from entering the irradiation chamber 40, and thereby limit air entry into the irradiation chamber to air taken in through air intake 352. The UV LEDs 416 may be positioned within the irradiation chamber 400 and the circular base 412 may be positioned on the outside of the irradiation chamber 400. The UV LEDs 416 are typically spaced from the walls of the irradiation chamber 400. An annular groove 414 formed in the circular base 412 of the UV LED apparatus 410 provides a channel between the irradiation chamber 400 and the air intake 408 formed in the body 310. Air intake 352, shown in FIG. 15, provides an opening in the first end cap 330 to the air intake 408 formed in the body 310. A channel is thus created for fluid communication from the outside of the ultraviolet air irradiation unit 300 to the inside.

Figure 18:
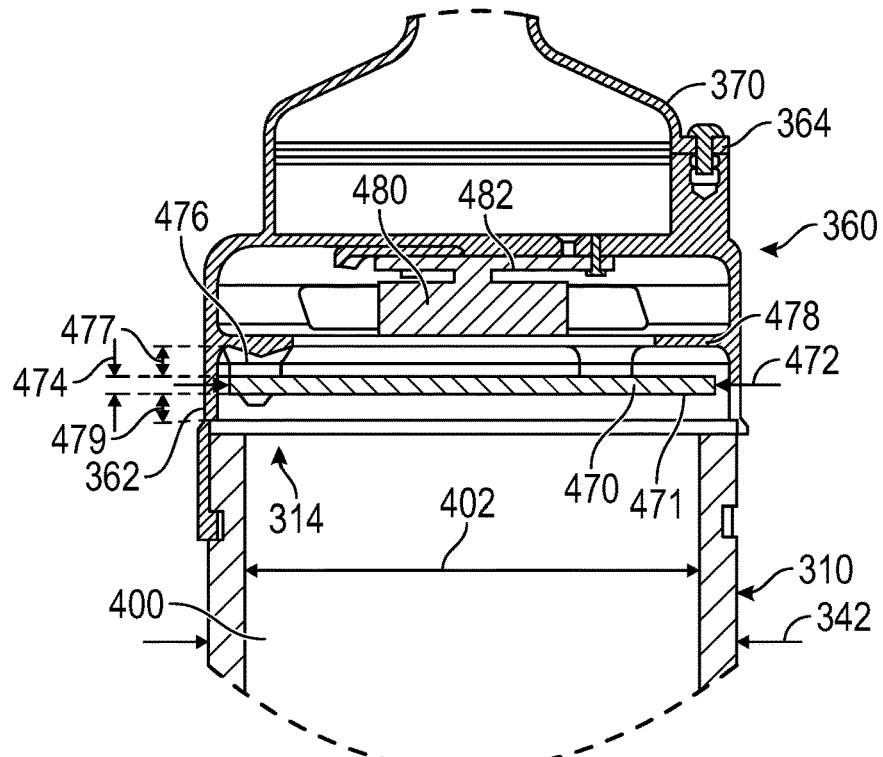
FIG. 18 is a close-up view of the referenced circled portion of FIG. 14.

Referring now to FIG. 18, a detailed view of portion 18 from FIG. 14 is depicted. Second end cap 360 may be configured to house reflection apparatus 470 and/or a pressure differential apparatus such as system fan 480. Second end cap 360 is configured to provide a closure to second open end 314 of the body 310. The reflection apparatus 470 may comprise a material having an ultraviolet radiation reflective surface 471 directed towards the interior of the irradiation chamber 400. The reflection apparatus 470 may have a diameter 472 and a thickness 474. The diameter 472 of the reflection apparatus 470 may be larger than the diameter 402 of the irradiation chamber 400, but smaller than the diameter of the body 310. This configuration allows the reflection apparatus 470 to overlap the opening of the irradiation chamber 400 but is small enough to provide a space between the reflector and the interior of the second end cap 360 to allow air to travel through the space. A reflector bracket 478 may be formed into the second end cap 360 and the reflection apparatus 470 may be attached to the reflector bracket 478 by spacers 476. The spacers 476 sets a distance 477 between the reflection apparatus 470 and the reflector bracket 478 and a distance 479 between the reflection apparatus 470 and the irradiation chamber 400 to allow air to travel through the spaces. The pressure differential apparatus, such as system fan 480, includes a bracket 482, which may be formed into the interior of the second end cap 360, which facilitates attachment of the pressure differential apparatus to the second end cap 360. The pressure differential apparatus provides adequate air flow required for the system and has the capability of variable air flow rates.

The ultraviolet air irradiation unit 300 is connected to the face mask 10 with the breathing tube 30 and allows for air to flow from the ultraviolet air irradiation unit 300 to the face mask 30. The filtered, if a HEPA filter is used, and irradiated air flows through the air outlet nipple 370 of the second end cap 360 by the pressure differential apparatus, such as system fan 480. The irradiated and, optionally, filtered air flows through the breathing tube 30 and into the face mask 20, both which may be sterilized. The irradiated and, optionally, filtered air is inhaled by the user and the face mask 20 exhausts the exhalation by the user. The face mask 20 may be sterile and is not exposed to the contaminated environment and thus may provide the user with filtered and irradiated air free of air particulates and neutralized of potentially harmful biological material.

The ultraviolet air irradiation unit 300, described in conjunction with FIGS. 15-17, irradiates air by passing air through the irradiation chamber 400. The pressure differential apparatus, such as system fan 480, pulls air through the air intake 352 of the first end cap. The incoming air flows from the air intake 352 to the internal air intake 408, which is formed in the body 310 and aligned with the air intake 352 of the first end cap 330. The air then flows from the internal air intake 408 through the channel created by the annular groove 414 formed in the circular base 412 of the UV LED apparatus 410. The air then flows from the channel through the space between the UV LEDs 416 and the walls of the irradiation chamber 400 to the irradiation chamber 400.

In an embodiment of the ultraviolet air irradiation unit 300, the UV LED apparatus 410 may include six UV LEDs 416 that are UV-C LEDs emitting UV radiation in the range of 260-270 nm, with each having an output power of 60 mW. The reflective surfaces of the irradiation chamber 400 and the reflection apparatus 470 takes advantage of the radiation pattern of the UV LEDs 416. By positioning the UV LEDs 416 perpendicular to the reflective material 406 of the irradiation chamber 400, the UV radiation emitted on the sides of the UV LEDs 416 are reflected back towards another wall. The total irradiance of the ultraviolet air irradiation unit 300 is approximately 10 mW/cm$^2$ along the length, with 6 seconds of exposure in the ultraviolet air irradiation unit 100 give approximately 60 mJ/cm$^2$, which eradicates approximately 99.99% of biological material in the air.

The purified air, which is filtered (if a HEPA filter is used) and irradiated, is then pulled around the reflection apparatus 470. The purified air is then pushed through the air outlet nipple 370 and into the breathing tube 30. The purified air is then pushed to the face mask 20 through the breathing tube 30 where the user is able to inhale the purified air. By placing a pressure differential apparatus, such as the system fan 480, at the outlet of the ultraviolet air irradiation unit 300, the pressure differential apparatus is able to compensate for any losses in air flow and pressure caused by the components of the ultraviolet air irradiation unit 300.

The ultraviolet air irradiation unit 300 provides positive air pressure to the face mask 20 to provide the user with comfortable breathing and to prevent the backflow of air into the ultraviolet air irradiation unit 300. The differential pressure provided by the ultraviolet air irradiation unit 300 coupled with an exit valve in the face mask 20 provides for that exhalations from the user exit the exit valve and out of the system. The ultraviolet air irradiation unit 300 may have a variable air flow rate to adapt to the users need. The ultraviolet air irradiation unit 200 and face mask 20 may also include a reversible function to purify the users exhale before purging it from the ultraviolet air irradiation system.

While the ultraviolet air irradiation system 10 of the present invention as herein shown and disclosed in detail is fully capable of obtaining the objects and providing the advantages herein before stated, it is to be understood that it is merely illustrative of embodiments of the invention and that no limitations are intended to the details of construction or design herein shown other than as described in the appended claims.

We claim:

1. A personal air irradiation system comprising:
   an inlet through which a flow of air enters into the personal aft irradiation system;

a chamber, configured as a cylinder, connected to the inlet such that the flow of air from the filter unit inlet enters the chamber, the chamber comprising an internal wall comprising a reflective material configured to reflect ultraviolet radiation, the chamber further comprising a plurality of ultraviolet light emitting diodes disposed at opposite ends of the chamber, the ultraviolet light emitting diodes configured to generate light in germicidal wavelengths and apply said light to the flow of aft in the chamber to produce a volume of irradiated air, the chamber further comprising an outlet through which the volume of irradiated air leaves the chamber;

an internal storage compartment disposed co-axially within the chamber, the storage compartment having a length equal to the length of the chamber;

a power source configured to energize the plurality of ultraviolet light emitting diodes, the power source disposed within a housing comprised by the internal storage compartment;

a tube attached to the outlet;

a face mask attached to the tube, wherein at least a portion of the volume of irradiated air flows from the chamber through the tube and into the face mask; and a pressure differential apparatus configured to cause the flow of air through the inlet, and the flow of the at least a portion of the irradiated aft through the tube and into the face mask.

2. The personal air irradiation system of claim 1 further comprising a filter unit connected to the inlet, the filter unit configured to receive the flow of air from the inlet before it enters the chamber.

3. The personal air irradiation system of claim 1 wherein the power source comprises a rechargeable battery.

4. The personal air irradiation system of claim 1 wherein the power source comprises 120 volts direct current.

5. The personal air irradiation system of claim 1 wherein the internal storage compartment is in a cylindrical configuration.

6. The personal air irradiation system of claim 1 wherein the internal storage compartment further comprises an external wall comprising the reflective material configured to reflect ultraviolet radiation.

7. The personal air irradiation system of claim 1 wherein the pressure differential apparatus comprises a fan connected to the inlet, the fan energized by the power source.

8. The personal air irradiation system of claim 1 wherein the pressure differential apparatus is configured to provide a variable flow rate.

9. The personal air irradiation system of claim 1 further comprising an oxygen concentration detector and a carbon dioxide concentration detector.

10. The personal air irradiation system of claim 1 wherein the reflective material is configured to reflect ultraviolet radiation having a range of wavelength of 100 to 400 nm.

11. A personal air irradiation system comprising an inlet through which a volume of air flows into the personal air irradiation system;

a chamber connected to the inlet, the chamber comprising an internal wall comprising a reflective material configured to reflect ultraviolet radiation, the chamber further comprising a first end wherein a first cap is attached to the first end, the first cap comprising a plurality of ultraviolet light emitting diodes configured to generate light in germicidal wavelengths, the chamber further comprising a second end wherein a second cap is attached to the second end, the second cap comprising a plurality of ultraviolet light emitting diodes configured to generate light in germicidal wavelengths, the chamber further comprising an outlet;

a power source configured to energize both pluralities of ultraviolet emitting diodes;

an internal storage compartment disposed co-axially within the chamber, the internal storage compartment having a length equal to the length of the chamber and comprising a housing for the power source;

a tube attached to the outlet;

a face mask attached to the tube; and a pressure differential apparatus configured to cause the volume of air to flow through the inlet and the chamber and the tube and into the face mask.

12. The personal air irradiation system of claim 11 wherein the first cap comprises a first set of four ultraviolet light emitting diodes and the second cap comprises a second set of four ultraviolet light emitting diodes.

13. The personal air irradiation system of claim 11 wherein the reflective material is configured to reflect ultraviolet radiation having a range of wavelength of 100 to 400 nm.

14. The personal air irradiation system of claim 1 wherein the chamber has a cylindrical configuration.

15. The personal air irradiation system of claim 11 wherein the internal storage compartment comprises a cylindrical configuration, the internal storage compartment further comprising an exterior wall comprising the reflective material, wherein the reflecting material on the interior wall of the chamber and the reflective material on the exterior wall of the internal storage compartment are cooperatively configured to increase the distribution of ultraviolet radiation within the chamber.

16. The personal air irradiation system of claim 11 wherein the pressure differential apparatus and the face mask are configured to selectively provide a reverse flow direction thereby causing exhalations from a user to flow from the face mask through the tube into the chamber wherein the exhalations are purified.

17. A method of irradiating a gas comprising the fallowing steps:

supplying the gas to an irradiation chamber by a pressure differential apparatus configured to selectively cause a flow of gas from the irradiation chamber to a face mask or from the face mask to the irradiation chamber, wherein the irradiation chamber comprises an internal wall comprising a reflective material and an internal storage irradiation chamber;

energizing the plurality of light emitting diodes to generate ultraviolet light in the wavelengths of 100-280 nm wavelengths and apply said ultraviolet light to the gas contained within the irradiation chamber, resulting in a volume of irradiated gas; and expelling the irradiated gas from the irradiation chamber.

18. The method of irradiating air a gas of claim 17 wherein the gas supplied to the irradiation chamber comprises air from the atmosphere.

19. The method of irradiating a gas of claim 18 wherein the air is first filtered through a HEPA filter before being supplied to the irradiation chamber.

20. The method of irradiating a gas of claim 17 wherein the gas supplied to the irradiation chamber comprises exhaled air from a person.

21. The method of irradiating a gas of claim 17 wherein the reflective material is configured to reflect ultraviolet radiation having a range of wavelength of 100 to 400 nm.

22. The method of irradiating a gas of claim 17 wherein an internal power source is contained within the irradiation chamber, wherein the internal power source energizes the plurality of light emitting diodes.

23. The method of irradiating a gas of claim 4 wherein the internal storage compartment further comprising an exterior wall comprising the reflective material wherein the reflective material of the internal wall of the irradiation chamber and the external wall of the internal storage compartment are cooperatively configured to increase the distribution of the ultraviolet light within the irradiation chamber.

24. The method of irradiating a gas of claim 17 wherein the irradiation chamber comprises a cylindrical configuration.

25. The method of irradiating a gas of claim 17 further comprising the step of controlling a volumetric flow rate of the gas and a flow direction through the irradiation chamber with an electronic control module attached to the irradiation chamber.

\* \* \* \* \*